(12) United States Patent
Chien et al.

(10) Patent No.: US 6,335,010 B1
(45) Date of Patent: Jan. 1, 2002

(54) GENE THERAPY IN CORONARY ANGIOPLASTY AND BYPASS

(75) Inventors: Shu Chien, La Jolla; John Y-J Shyy, San Diego, both of CA (US)

(73) Assignee: University of California at San Diego, La Jolla, CA (US)

(*) Notice: Subject to any disclaimer, the term of this patent is extended or adjusted under 35 U.S.C. 154(b) by 0 days.

(21) Appl. No.: 08/884,866

(22) Filed: Jun. 30, 1997

Related U.S. Application Data

(60) Provisional application No. 60/030,358, filed on Nov. 8, 1996.

(51) Int. Cl.⁷ ............................................. A61K 48/00
(52) U.S. Cl. ..................... 424/93.2; 514/44; 435/320.1; 435/455
(58) Field of Search .......................... 424/932; 435/320, 435/455, 458; 514/44; 536/23.1

(56) References Cited

U.S. PATENT DOCUMENTS

| | | | | |
|---|---|---|---|---|
| 5,242,397 A | * | 9/1993 | Barath et al. ................. | 604/96 |
| 5,328,470 A | * | 7/1994 | Nabel et al. ................. | 604/101 |
| 5,552,309 A | * | 9/1996 | March ......................... | 435/455 |
| 5,562,922 A | | 10/1996 | Lambert ....................... | 424/486 |
| 5,660,855 A | * | 8/1997 | Male-Brune ................... | 424/450 |
| 5,698,531 A | * | 12/1997 | Nabel et al. ................. | 514/44 |
| 5,707,969 A | * | 1/1998 | Nabel et al. ................. | 514/44 |
| 5,792,453 A | * | 8/1998 | Hammond et al. .............. | 424/93.21 |
| 5,851,521 A | * | 12/1998 | Branellec et al. ............ | 424/93.2 |
| 5,879,713 A | * | 3/1999 | Roth et al. .................. | 424/489 |
| 5,880,102 A | * | 3/1999 | George et al. ................ | 514/44 |
| 5,981,487 A | * | 11/1999 | Koch et al. .................. | 514/12 |
| 6,114,311 A | * | 9/2000 | Parmacek et al. ............. | 514/44 |

FOREIGN PATENT DOCUMENTS

| | | | |
|---|---|---|---|
| WO | WO 93/09236 | | 5/1993 |
| WO | WO 95/25807 | * | 9/1995 |

OTHER PUBLICATIONS

Ohno et al., Gene Therapy for Vascular Smooth Muscle Cell Proliferation After Arterial Injury, Aug. 1994, Science, vol. 265, pp. 781–784.*
Ngo et al., in The Protein Folding Problem and Tertiary Structure Prediction, Merz et al., (ed.), Birkhauser, Boston, MA, pp. 492–495, 1994.*
Indofi et al. (Basis Research in Cardiology, 92, 6, pp. 378–84), 1997.*
Anderson, Nature, vol. 392, 25–30, 1998.*
Gunzburg et al., vol. 1, No. 9, pp. 410–417, 1995.*
Mastrangelo et al.(Seminars in Oncology, vol. 23, No. 1, pp. 4–21), 1996.*
Meng et al. (Gene Therapy of Cancer, Chapter 1, pp. 3–20), 1999.*
Tait et al. (Clinical Cancer Res., vol. 5, 1707–1714), 1999.*
Indolfi et al. (Nature Medicine, vol. 1, pp. 541–515), 1995.*
Ueno et al. (Arteriosclerosis, Thrombosis, and Vascular Biology, 17, 5, pp. 898–904), May 1997.*
Taparowsky et al. (Cell, 34, pp. 581–586, 1983.*
"Remington's Pharmaceutical Science," 1990, 18th ed., Mack Publishing Co., Easton, PA.
Angel and Karin, "The role of Jun, Fos and the AP–1 complex in cell–proliferation and transformation" *Biochimica et Biophysica Acta* 1072:129–157 (1991).
Ausubel et al., Current Protocols in Molecular Biology, Greene Publishing Associates and Wiley Interscience, N.Y. (1989).
Bogoyevitch et al., "Stimulation of the Stress–Activated Mitogen–Activated Protein Kinase Subfamilies in Perfused Heart, p38/RK Mitogen–Activated Protein Kinases and c–June N–Terminal Kinases Are Activated by Ischemia/Reperfusion" *Circ Res.* 79:162–173 (1996).
Boguski and McCormick, "Proteins regulating Ras and its relatives" *Nature* 366:643–654 (1993).
Capecchi, M. R., "High Efficiency Transformation by Direct Microinjection of DNA into Cultured Mammalian Cells" *Cell* 22:479–488 (1980).
Chardin et al., "Human Sos1: A Guanine Nucleotide Exchange Factor for Ras That Binds to GRB2," *Science* 260:1338–1343 (1988).
Chen and Okayama, "High–Efficiency Transformation of Mammalian Cells by Plasmid DNA" *Molecular and Cellular Biology* 7(8):2745–2752 (1987).
Chu et al., "Electroporation for the efficient transfection of mammalian cells with DNA" *Nucleic Acids Research* 15(3):1311–1327 (1987).
Cobb et al., "Extracellular signal–regulated kinases: ERKs in progress" *Cell Regulation* 2:965–978 (1991).
Coso et al., "The Small GTP–Binding Proteins Rac1 and Cdc42 Regulate the Activity of the JNK/SAPK Signaling Pathway" *Cell* 81:1137–1146 (1995).

(List continued on next page.)

*Primary Examiner*—Dave T. Nguyen
(74) *Attorney, Agent, or Firm*—Gray Cary Ware & Freidenrich LLP; Lisa A. Haile; Sheila Kirschenbaum

(57) ABSTRACT

Hemodynamic forces play a key role in inducing 2, theroscler-osis-implicated gene in Vascular endothelial cells. To ellcitate the signal transduction pathway leading to such gene expression, the effects of fluid shearing on the activities of upstream signaling molecules is reported here. Fluid shearing (shear stress=12 dynes/cm$^2$) induced a transient and rapid activation of p21$^{ras}$ and preferentially activated c-jun NH$_2$ terminal kinases (JNK 1, 2) over extracellular signal-regulated kinases (ERK-1, -2). Co-transfection of RasNI7, a dominant negative mutant of Ha-Ras, attenuated the shear-activated JNK and luciferase reporters driven by TPA-responsive elements. JNIK(K-R) and MEKK(K-M), the respective catalytically inactive mutants of JNKI and MEKK, also partially inhibited the shear-induced luciferase reporters. In contrast, Raf301, ERK(K71R), and ERK (K52R), the dominant negative mutants of Raf-1, ERK-1, and ERK-2, respectively, had little effects on the activities of these reporters. The activation of JNK was also correlated with an increased c-Jun transcriptional activity, which was attenuated by a negative mutant of Son of sevenless (Sos). Thus, mechanical stimulation exerted by fluid shearing activates, primarily the Ras-MEKK-JNK pathway in inducing endothelial gene expression.

5 Claims, 14 Drawing Sheets

OTHER PUBLICATIONS

Curiel et al., "Gene Transfer to Respiratory Epithelial Cells via the Receptor–mediated Endocytosis Pathway" *American Journal of Respiratory Cell and Molecular Biology* 6:247–252 (1992).

Davies et al., "Quantitative Studies of Endothelial Cell Adhesion" *The American Society for Clinical Investigation, Inc.* 93:2031–2038 (1994).

Davies, Peter F., "Flow–Mediated Endothelial Mechanotransduction" *Physiological Reviews* 75(3):519–560 (1995).

Deng and Karin, "c–Fos transcriptional activity stimulated by H–Ras–activated protein kinase distinct from JNK and ERK" *Nature* 371:171–175 (1994).

Dérijard et al., "JNK:1 A Protein Kinase Stimulated by UV Light and Ha–Ras That Binds and Phosphorylates the c–Jun Activation Domain" *Cell* 76:1025–1037 (1994).

DeVries–Smits et al. "Involvement of p21$^{ras}$ in Activation of Extracellular Signal–Regulated Kinase 2" *Nature* 357:602–604 (1992).

Downward et al., "Stimulation of p21$^{ras}$ upon T–cell activation" *Nature* 346:719–723 (1990).

Egan et al., "Association of Sos Ras exhange protein with Grb2 is implicated in tyrosine kinase signal transduction and transformation" *Nature* 363:45–51 (1993).

Feig and Cooper, "Inhibition of NIH 3T3 Cell Proliferation by a Mutant ras Protein with Preferential Affinity for GDP" *Molecular and Cellular Biology* 8(8):3235–3243 (1988).

Felgner and Ringold, "Cationic liposome–mediated transfection" *Nature* 337 (26):387–388 (1989).

Felgner et al., "Lipofection: A highly efficient, lipid–mediated DNA–transfection procedure" *Proc. Natl. Acad. Sci. USA* 84:7413–7417 (1987).

Frangos et al. "Flow Effects of Prostacyclin Production by Cultured Human Endothelial Cells" *Science* 227:1477–1479 (1985).

Frost et al., "A requirement for extracellular signal–regulated kinase (ERK) function in the activation of AP–1 by Ha–Ras, phorbol 12–myristate 13–acetate, and serum" *Proc. Natl. Acad. Sci. USA* 91:3844–3848 (1994).

Galcheva–Gargova et al., "An Osmosensing Signal Transduction Pathway in Maammalian Cells" *Science* 265:806–808 (1994).

Gille et al., "Phosphorylation of transcription factor p62$^{TCF}$ by MAP kinase stimulates ternary complex formation at c–fos promoter" *Nature* 358:414–417 (1992).

Gómez–Foix et al., "Adenovirus–mediated Transfer of the Muscle Glycogen Physophorylase Gene into Hepatocytes Confers Altered Regulation of Glycogen Metabolism" *The Journal of Biological Chemistry* 267 (35): 25129–25134 (1992).

Hibi et al., "Identification of an oncoprotein– and UV–responsive protein kinase that binds and potentiates the c–Jun activation domain" *Genes & Development* 7:2135–2148 (1993).

Hill and Treisman, Transcriptional Regulation by Extracellular Signals: Mechanisms and Specificity *Cell* 80:199–211 (1995).

Hsieh et al., "Pulsatile and Steady Flow Induces c–fos Expression in Human Endothelial Cells" *Journal of Cellular Physiology* 154:143–151 (1993).

Hsieh et al., "Shear–Induced Platelet–Derived Growth Factor Gene Expression in Human Endothelial Cells Is Mediated by Protein Kinase C" *Journal of Cellular Physiology* 150:552–558 (1992).

Indolfi et al., "Inhibition of cellular ras prevents smooth muscle cell proliferation after vascular injury in vivo" *Nature Medicine* 1(6):541–545 (1995).

Isner et al, "Arterial Gene Transfer for Therapeutic Angiogenesis in Patients With Peripheral Artery Disease" *Hum Gen Ther* 7:959–988 (1996).

Joneson and Bar–Sagi, "Ras effectors and their role in mitogenesis and oncogenesis" *J Mol Med* 75:587–593 (1997).

Kim et al., "The TRE–Mediated Gene Expression in Response to Shear Stress Involves SH2–Containing Molecules," *FASEB J.,* 10:A24 (1996).

Kolch et al., "Raf–1 protein kinase is required for growth of induced NIH/3T3 cells" *Nature* 349:426–428 (1991).

Kuchan et al., "Role of G proteins in shear stress–mediated nitric oxide production by endothelial cells" *The American Physiological Society* 267:C753–C758 (1994).

Lange–Carter and Johnson, "Ras–Dependent Growth Factor Regulation of MEK Kinase in PC12 Cells" *Science* 265:1458–1461 (1994).

Lee et al., "A protein kinase involved in the regulation of inflammatory cytokine biosynthesis" *Nature* 372:739–746 (1994).

Lin et al., "Identification of a Dual Specificity Kinase That Activates the Jun Kinases and p38–Mpk2" *Science* 268:266–290 (1995).

Maniatis et al., Molecular Cloning: A Laboratory Manual, Cold Spring Harbor Laboratory, N.Y. (1989).

Marias et al., "The SRF Accessory Protein Elk–1 Contains a Growth Factor–Regulated Transcriptional Activation Domain" *Cell* 732:381–393 (1993).

Marshall, C. J., "Specificity of Receptor Tyrosine Kinase Signaling: Transient versus Sustained Extracellular Signal–Regulated Kinase Activation" *Cell* 80:179–185 (1995).

Mayer et al., "A novel oncogene with structural similarity to phospholipase C" *Nature* 332 (17):272–275 (1988).

McGrory et al., "A Simple Technique for the Resuce of Early Region I Mutations into Infectious Human Adenovirus Type 5" *Virology* 163:614–617 (1988).

Medema et al., "Two Dominant Inhibitory Mutants of p21$^{ras}$ Interfere with Insulin–Induced Gene Expression" *Molecular and Cellular Biology* 11(12):5963–5967 (1991).

Miller, D. A., "Human gene therapy comes of age" *Nature* 357:455–460 (1992).

Minden et al., "c–Jun N–Terminal Phosphorylation Correlates with Activation of the JNK Subgroup but Not the ERK Subgroup of Mitogen–Activated Protein Kinases" *Molecular and Cellular Biology* 14(10):6683–6688 (1994).

Minden et al., "Differential Activation of ERK and JNK Mitogen–Activated Protein Kinases by Raf–1 and MEKK" *Science* 266:1719–1723 (1994).

Minden et al., "Selective Activation of the JNK Signaling Cascade and c–Jun Transcriptional Activity by the Small GTPases Rac and Cdc42Hs" *Cell* 81:1147–1157 (1995).

Morooka et al., "Ischemia and Reperfusion Enhance ATF–2 and c–Jun Binding to cAMP Response Elements and to an AP–1 Binding Site from the c–jun Promoter" *The Journal of Biological Chemistry* 270(50):30084–30092 (1995).

Mulligan, R. C., "The Basic Science of Gene Therapy" *Science* 260:926–932 (1993).

Pawson and Schlessinger, "SH2 and SH3 domains" *Current Biology* 3(7):434–442 (1993).

Ponting and Bork, "Pleckstrin's repeat performance: a novel domain in G–protein singaling?" *TIBS* 21:245–246 (1996).

Robbins et al., "Regulation and Properties of Extracellular Signal–regulated Protein Kinases 1 and 2 in Vitro" *The Journal Of Biological Chemistry* 268(7):5097–5106 (1993).

Rozengurt, E., "Growth factors and cell proliferation" *Current Opinion in Cell Biology* 4:161–165 (1992).

Russell et al., "Direct Interaction between Ras and the Kinase Domain of Mitogen–activated Protein Kinase Kinase Kinase (MEKK1)" *The Journal of Biological Chemistry* 270(20):11757–11760 (1995).

Sadowski et al., A Noncatalytic Domain Conserved among Cytoplasmic Protein–Tyrosine Kinases Modifies the Kinase Function and Transforming Activity of Fujinami Sarcoma Virus P130$^{gag-fps}$ *Molecular and Cellular Biology* 6(12):4396–4408 (1986).

Sakaue et al., "A Dominant–Negative Mutant of mSOS1 Inhibits Insulin–Induced Ras Activation and Reveals Ras- –Dependent and –Independent Insulin Signaling Pathways" *Molecular and Cellular Biology* 15(1):379–388 (1995).

Shyy and Chien, "Role of integrins in cellular responses to mechanical stress and adhesion" *Current Opinion in Cell Biology* 9:707–713 (1997).

Shyy et al., "Fluid shear stress induces a biphasic response of human monocyte chemotactic protein 1 gene expression in vascular endothelium" *Proc. Natl. Acad. Sci. USA* 91:4678–4682 (1994).

Sluss et al., "Signal Transduction by Tumor Necrosis Factor Mediated by JNK Protein Kinases" *Molecular and Cellular Biology* 14(12):8376–8384 (1994).

Stokoe et al., "Activation of Raf as a Result of Recruitment to the Plasma Membrane" *Science* 264:1463–1467 (1994).

Su et al., "JNK Is Involved in Signal Integration during Costimulation of T Lymphocytes" *Cell* 77:727–736 (1994).

Thomas et al., "Ras Is Essential for Nerve Growth Factor–and Phorbol Ester–Induced Tyrosine Phosphorylation of MAP Kinases" *Cell* 68:1031–1040 (1992).

Traverse et al., "Sustained activation of the mitogen–activated protein (MAP) kinase cascade may be required for differentiation of PC12 cells" *Biochem. J.* 288:351–355 (1992).

Wang et al., "Mechanotransduction Across the Cell Surface and Through the Cytoskeleton" *Science* 260:1124–1127 (1993).

Wiesmüller and Wittinghofer, "Signal Transduction Pathways Involving RAS Mini Review" *Cellular Signaling* 6(3):247–267 (1994).

Yan et al., "Activation of stress–activated protein kinase by MEKK1 phosphorylation of its activator SEK1" *Nature* 371:798–800 (1994).

Yang et al., "In vivo and in vitro gene transfer to mammalian somatic cells by particle bombardment" *Proc. Natl. Acad. Sci. USA* 87:9568–9572 (1990).

Ye et al., "Improved Bioresorbable Microporous Intravascular Stents for Gene Therapy" *ASAIO Journal* 42:M823–M827 (1996).

* cited by examiner 495051
1 ATGACGGAATATAAGCTGGTGGTGGTGGGCGCCGGCGGTGTGGGCAAAAATGCGCTGACCATCCAGCTGATCCAGAACCA
TTTGTGGACGAATACGACCCCACTATAGAGGATTCCTACCGAAGCAGCAGGTGGTCATTGATGGGGAGACGTGCCTGTTGG
ACATCCTGGATACCGCCGGCCTGGAGGAGTACAGCGCCATGCGGGACCAGTCAATGCGCACCGGGGAGGGCTTCCTGTGT
GTGTTTGCCATCAACAACACCAAGTCTTTTGAGGACATCCACCAGTACAGGGAGCAGATCAAACGGGTGAAGGACTCGGA
TGACGTGCCCATGGTGCTGGTGGGAACAAGTGTGACCTGGCTGCACGCCACTGTGGAATCTCGGCAGGCTCAGGACCTCG
CCCGAAGCTACGGCCATCCCCTACATCGAGAGCCTCGGCCAAGACCCGGCAGGAGTGCCTTCTACACGTTGGTG
CGTGAGATCCGGCAGCACAAGCTGCGAACCCTCCTGATGAGAGTGGCCCCGGCTGCCTCATGAGCTGCAAGTGTGT
GCTCTCCTGA 3'

FIG. 11

17
1 MTEYKLVVVGAGGVGKNALTIQLIQNHFVDEYDPTIEDSYRKQVVIDGETCLLDILDTAGLEEYSAMRDQSMRTGEGFLC
5' VFAINNTKSFEDIHQYREQIKRVKDSDDVPMVLVGNKCDLAARTVESRQAQDLARSYGIPYIETSAKTRQGVEDAFYTLV
REIRQHKLRKLNPPDESGPGCMSCKCVLSZ 3'

FIG. 12

Selection of Gene Transfer Method using Marker Gene LacZ
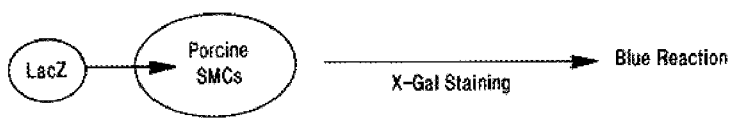
5% Efficiency By Liposomes
100% Efficiency By Adenovirus
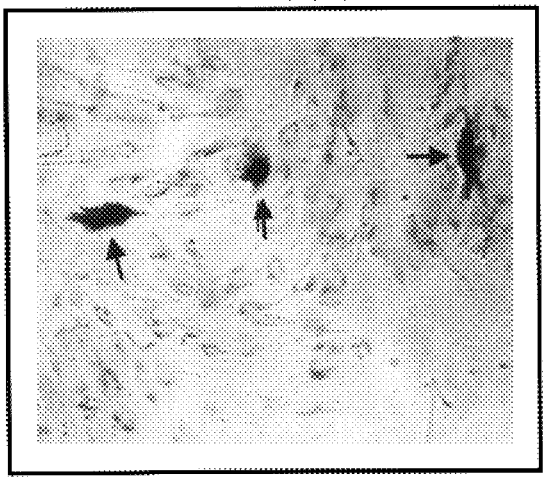
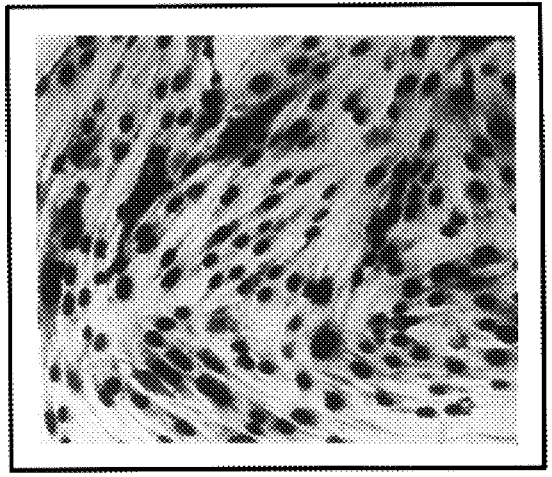
FIG. 13A
FIG. 13B

GENE THERAPY IN CORONARY ANGIOPLASTY AND BYPASS

The present application claims priority to Provisional Application U.S. Ser. No. 60/030,358, filed Nov. 8, 1996.

The government owns rights in the present invention pursuant to grant numbers HL 19454 and HL 43026 from NIH e.g., the National Institutes of Health).

BACKGROUND OF THE INVENTION

Vascular endothelial cells (ECs), located at the interface between the blood and the vessel wall, are exposed to the mechanical environment resulting from hemodynamic activities. Fluid shear stress is the hemodynamic force acting tangentially on the vascular ECs and it plays significant roles in atherogenesis and reperfusion injury. Many genes encoding for growth factors (e.g., platelet derived growth factor and transforming growth factor β-1), vasoconstrictors (e.g., endothelin-1), vasodilators (e.g., nitric oxide synthase), adhesion molecules (e.g., intercellular adhesion molecule-1, ICAM-1), and monocyte chemoattractants (e.g., monocyte chemotactic protein-1, MCP-I) in the ECs are modulated by fluid shearing (see7 for review). The induction of some, and perhaps the majority, of these inflammation-related genes is rapid and transient, and de novo protein synthesis is not required. These are the characteristics of the expression of immediate early (IE) genes induced by mitotic factors and agonists. The phorbol ester 12-0-tetradecanoyl-13-phorbol-acetate (TPA) responsive element, TRE, mediates the expression of many IE genes through its interaction with the transcription factor AP-1, a Jun/Fos heterodimer or a Jun/Jun homodimer (1). A divergent TRE in the 5' promoter region of the MCP-1 gene has been found by the present inventors to be responsible for its mechanical inducibility (41). Consensus TRE with the sequence TGACTACA is sufficient for the shear-induced reporter activities in different types of cells. The applied fluid shearing probably exerts its actions on the cellular membrane to initiate biochemical signals which can then be transduced through the cytoplasm into the nucleus where the activation of AP-I/TRE occurs.

A major process through which extracellular stimuli can be transmitted into cells involves the membrane-associated $p21^{ras}$ and its downstream cytoplasmic kinase pathways, especially the members in the mitogen-activated protein kinases (MAPK) family. $p21^{ras}$ is a small GTPase molecule that plays a key role in the signal transduction pathways of cellular responses to stimuli by mitogins, cytokines, environmental stresses, and UV irradiation. $p21^{ras}$ cycles between an active GTP-bound state and an inactive GDP-bound state, thereby functioning as a molecular switch in response to extracellular stimuli in the control of normal and transformed cell growth. Activated $p21^{ras}$ triggers two protein kinases, Raf-1 and MEK (MAPK kinase) kinase (MEKK) which activate the downstream MAPKs, including c-Jun NH2-terminal kinases (JNK) and extracellular signal-regulated kinases ERK (11,32). Raf-1 activates ERK but not JNK, whereas MEKK mediates preferentially JNK over ERK (32,48). In different types of cells in response to UV irradiation, Ha-Ras expression, and osmotic shock, JNK kinase (JNKK) activates JNK by phosphorylating the Thr-Pro-Tyr phosphorylation sites, and the activated JNIK binds to c-Jun to specifically phosphorylate the -63 and -73 amino acids at the N-terminal (10, 29). In response to Ha-Ras expression, serum growth factor, or phorbol ester TPA stimulation, MEK activates ERK which in turn phosphorylates the transcription factor p62 ternary complex factor (p62TCF), leading to the activation of c-Fos (5, 18, 30, 37). In R.EF-52 fibroblasts, the activation of AP-I/TRE by these stimuli is mediated through ERK (16). It is not known where and how mechanical stimuli are transduced to biochemical signals. $p21^{ras}$ is a membrane-associated protein and its activation of the downstream Raf-1 and MEKK is through direct interactions on the membrane (27, 28, 36, 38, 43). Wang et al. (47) suggest that the integrins on the basal membrane constitute a mechano-receptor and that stress fibers are necessary to transmit the applied forces. Similarly, Davies et al. (8) suggest that focal adhesion complex at the abluminal endothelial membrane are mechanically responsive elements coupled to the cytoskeleton.

Ras can activate both ERK and JNK pathways (27, 32). The signaling in response to growth factors such as epidermal growth factor (EGF) and nerve growth factor (NGF) is mediated through both the Ras/ERK and Ras/JNK pathways in PCI2, MRCS, and HeLa cells (32, 33). In contrast, inflammation—related cytokines (e.g., TNF and IL-1), environment stresses (e.g., osmoic pressure), and UV irradiation selectively activate the Ras/JNK, but not the ERK, pathway (17, 19, 26, 32, 42, 44). Mechanical shearing is a form of force borne by vascular ECs and many other cell types, such as the osteoblasts, under physiological conditions. The application of such physiological forces on static cells cultured in the flow chambers provides a sudden change of hemodynamic environment. This in vitro system mimics the pathophysiological changes during reperfusion after flow stoppage. Fluid shearing of vascular EC caused the activation of JNK by more than 10-fold and the activation of ERK by a much lesser magnitude (1.8 fold) and shorter duration (FIG. 3). Morooka et al. demonstrated that reperfusion of ischemic kidney induced a rapid activation of JNK (35). Bogoyevitch et al. reported that reperfusion of rat heart induced a 10- to 50-fold activation of JNK, but not ERK (2).

SUMMARY OF THE INVENTION

While several laboratories have shown that fluid shearing induces a variety of transient responses in the endothelial cytoplasm and nucleus, there is little, if any, knowledge on how ECs transduce the mechanical stimuli into biochemical signals which ultimately activate the downstream gene expression. The present inventors have found that fluid shearing, a physiological form of hemodynamic forces, activates $p21^{ras}$ in ECs in a rapid and transient manner, and that it is followed by the activation of the MEKK-JNK pathway, leading to the induction of the AP-1/TRE mediated gene expression in the nucleus. In contrast, the ERK pathway is weakly activated by fluid shearing and is not essential for the shear-induced activation of AP-I/TRE. These results indicate that hemodynamic forces share the same signaling pathways as a variety of stimuli, including osmotic pressure, chemical stress, and UV irradiation, in activating the promoter regions of IE genes.

Percutaneous transluminal coronary angioplasty (PTCA) causes restenosis mainly from proliferation of vascular smooth muscle cells (VSMC) gene expression and proliferation. Recognizing this, an effective gene therapy method for the reduction of the high incidence of restenosis after angioplasty is provided in the present invention.

The present invention demonstrates that $p21^{ras}$ plays critical roles in the responses of vascular ECs to fluid shearing. First, the guanine nucleotide exchange on Ras, i.e., the conversion of Ras-GDP to Ras-GTP, was promoted by fluid shearing. Second, the dominant negative mutant of $p21^{ras}$ RasN17, inhibited the shear-induced signal transduction pathway including JNK and its downstream c-Jun transcriptional activity. Third, RasNI7 also abrogated the reporter activities of 4×TRE-Luc and MCP1-Luc-540, two chimeric constructs whose induction by fluid shearing is mediated by AP-1/TRE (41). The present inventors establish that the mechanical-biochemical transmitting process occurs at least in part on the cellular membrane. The present inventors propose that the signals initiated by fluid shearing originate from the abluminal side of ECs. In contrast, the burst production of nitric oxide is dependent upon the activation of G proteins (25) which are located at the luminal surface.

Besides the activation of ERK, the inventors also demonstrate that the blockage of the $p21^{ras}$-RAF-ERK pathway by Raf.301, K7 I R, or K52R did not affect the TRE-mediated reporter activities in response to fluid shearing (FIG. 6). In contrast, the blockade of the $p21^{ras}$-MEKK-JNK pathway by either MEKK(K-M) or JNK(K-R) significantly attenuated the shear induced reporter activities (FIG. 5). MEKK(K.M) and JN.K(K-R), which were mutated at the ATP binding sites with the conserved Lys replaced by either a Met or an Arg, act like dominant negative mutants of .MEKK and JNK, respectively (32; unpublished results of B. Su). Thus, the induction of MEKK-JNK by fluid shearing plays a key role for the activation of the downstream AP1/TRE, an effect which is probably mediated through c-Jun. On the other hand, the activation of cFos, which is dependent on ERK/TCF (9), seems to be not necessary for such an activation. It appears that the Jun-Jun homodimer, rather than the Jun-Fos heterodimer, serves as the activator in this shear-elicited signal transduction pathway. Presumably, the shear-induced activation of JNK by JNKK phosphorylates the pre-existing, latent c-Jun in the cytoplasm, and this is followed by the translocation of the activated c-Jun into the nucleus where the Jun-Jun homodimer activates the target gene by interacting with TRE. Transactivation assays using RSV-Jun, an expression plasmid encoding c-Jun, showed similar effects as fluid shearing, indicating the MCP1-Luc-540 is activated by JNK (41). These results, taken together, suggest that the $p21^{ras}$ .MEKK-JNKK-JNK pathway is necessary and sufficient to activate the AP-1/TRE-mediated gene expression in ECs in response to fluid shearing (FIG. 8). In addition to the phosphorylation of the pre-existing c-Jun, the induction of AP-1 activity may also occur at the transcriptional level. Mechanical shearing induces c-jun mRNA and it remains at an elevated plateau level for at least 4 hr (21). It is not known whether the activated JNK in the sheared cells would activate the de novo synthesized c-Jun through the phosphorylation of Ser-63 and -73 (33), and if it does, what would be duration over which the activated c-Jun homodimer can activate the downstream genes.

The duration of MAPK activation by different extracellular stimuli may determine whether the cells can elicit differentiation or proliferation responses (31). In PCI2 cells, ERK activation is sustained for several hours following NGF stimulation, thus leading to differentiation of these cells to become sympathetic neurons. In contrast, the response is transient after EGF stimulation, and the result is proliferation rather than differentiation (45). Whether the activation is sustained or transient is dependent on the receptor tyrosine kinases (RTKs) which activate $p21^{ras}$. The cellular responses to fluid shearing, including the activation of $p21^{ras}$, JNK and the downstream IE genes (e.g., the MCP-1 gene), are all transient and rapid. The cells are conceivably desensitized by the applied mechanical force following the initial activation.

The present inventors have found that pre-shearing desensitizes ECs against further TPA-induced ERK phosphorylation (41). Such mechanically induced transient responses and desensitization have their physiological significance in vascular ECs. Serving as the barrier between blood and vessel wall, these cells need a desensitization mechanism to protect them from the continuous stimulation imposed by the hemodynamic forces. In bends and bifurcations where the shearing forces are low and the blood flow is disturbed, there may not have been the same degree of desensitization as that in the lesion resistant areas where the endothelium is subjected to a relatively constant laminar flow with high shearing forces. When cumulated over years, the small differences in the mechanical environment (i-e., the magnitude of shearing forces and flow pattern) between the cells in these different regions may have considerable pathophysiological consequences.

It is intriguing that Sos can be upstream to the fluid shearing-activated $p21^{ras}$. The present inventors have found that the negative mutants of GTb2 and Sos can also partially block the shear-induced 4×TRE-P1 luc and MCPI-luc-540 in BAEC (23). Grb2 is an adapter protein which contains one src homology domain 2 (SH2) and two SH3 domains. GTb2 binds to Sos, a guanine nucleotide exchange factor specific to $p21^{ras}$. Thus, the upstream mechanisms by which the mechanobiochemical transduction activates Ras pathway may be similar to those for growth factor stimuli. It remains to be investigated how common upstream signals diverge to activate JNK (mechanical stimuli) and ERK (growth factor).

The $p21^{ras}$-MEKK-JNK-AP-1/TRE pathway provides a molecular mechanism for the signal transduction in endothelial responses to mechanical stimulation. RTKs may be the "mechanical force receptors/sensors" on the membrane that execute the mechano-biochemical transduction to activate such a pathway. The similarity between fluid shearing and EGF in inducing endothelial responses including the involvement of SH2-containing molecules such as Grb2 suggests that RTK, especially EGF receptor subfamily, may play an important role to transduce the mechanical stimuli into biochemical signals. Recently, it has been shown that the small GTP-binding proteins Rac and Cdc42 are upstream to JNK (6, 34). Constitutively activated Rac and Cdc42 stimulate the catalytic activity of JNK (34). Dominant negative mutants of Rac and Cdc42 effectively reduce the EGF-activated JNK (6). Thus, Rac and Cdc42 are crucial intermediates in the signaling pathway leading from activated RTKs to JNK. These findings reinforce the hypothesis that RTKs are candidates for the mechanical force sensor, but direct experimental evidence is still lacking. Whatever the sensor mechanism, the $p21^{ras}$-MEKK-JNK-AP-1/TRE pathway seems to be part of a coordinated programming, including other possible components such as G proteins, $Ca^{2+}$, integrins, etc. The synergism and/or cross communication among these different signaling pathways probably plays significant roles in constituting the endothelial responses to hemodynamic forces.

The present invention in one aspect provides for a method of inhibiting or reducing tissue injury attendant to angioplasty through the introduction of a Ras therapeutic gene capable of blocking a Ras signal transduction pathway. In some embodiments, the method comprises introducing a Ras therapeutic gene capable of blocking a Ras signal transduction pathway. By way of example, and not exclusion, the Ras signal transduction pathway that is to be blocked as part of the method is selected from the group consisting of an MEKK pathway, a JNKK pathway, an ERK pathway, and an MEK pathway. These pathways are among those contemplated by the present inventors to be useful in blocking Ras expression.

In particular embodiments, the Ras therapeutic gene is more particularly described as a Ras mutant gene, and even more particularly as a dominant negative mutant Ras gene. In some embodiments, the method contemplates the delivery of this gene and of the Ras therapeutic gene more generally, in adenovirus. However, it is contemplated that any variety of carrier vehicles may be used in the delivery of the gene, including via plasmid, retrovirus, adenovirus or any other molecule capable of effectively providing the therapeutic gene or a portion thereof to a population of cells targeted for treatment.

Methods for introducing foreign genetic material into a cell are well known to those of skill in the art, and said standard protocols for introducing a gene of interest into a cell are contemplated by the present inventors as within the scope of the present invention.

In another aspect, the invention provides a method for reducing restenosis employing the Ras therapeutic gene described herein, or a therapeutically functional fragment thereof. In some embodiments, the method comprises administering to a patient at risk of restenosis a therapeutic Ras gene, particularly within an adenovirus. Such adenovirus is preferably replication defective, and will include a substituted E1 region. In some embodiments, the adenoviral construct will comprise a Ras N17 adenovirus package, wherein the Ras N17 adenovirus package is a non-replicating adenovirus genome containing a Ras N17 expression cassette.

In yet another aspect, the invention provides a therapeutic composition comprising a replication deficient recombinant adenovirus construct comprising a therapeutic Ras gene as described herein.

In other potential applications, the prevention and treatment of restenosis in other conditions, e.g., arterio-venous grafts used in hemodialysis and intra-hepatic portal-caval shunts used in portal hypertension. Other possible applications are for the inhibition of smooth muscle proliferation in smooth muscle tumors of the uterus and other organs.

As used in the description of the present invention, the term "a" is intended to mean one or more.

Other applications and uses of the present invention not specifically articulated herein are intended as within the scope of the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 10A shows the section from a normal rat without balloon injury; FIG. 10B shows the section after balloon injury without Ad-RasN17 treatment; FIG. 10C shows the section after balloon injury plus treatment with Ad-RasN17. The arteries were removed 14 days after angioplasty.

FIG. 11. Nucleic acid sequence RasN17. The underlined triplet, AAT, is the site of substitution for the 17-mutants described in the present application.

FIG. 12. Amino acid sequence RasN17. The underlined "N" at position 17 indicates the site of substitution for the mutant Ras proteins of the present invention.

FIG. 13A and FIG. 13B. Comparison of the relative efficiency of RasN17 gene transfer using liposomes (13A) and adenovirus (13B). RasN17 was co-transfected with the marker gene LacZ into porcine smooth muscle cells. The % success in LacZ transfection can be detected by the use of X-gal staining which causes the formation of a blue color. The efficiency was only 5% with the use of liposomes, but 100% with adenovirus.

DETAILED DESCRIPTION OF THE PREFERRED EMBODIMENTS

Figure 1:
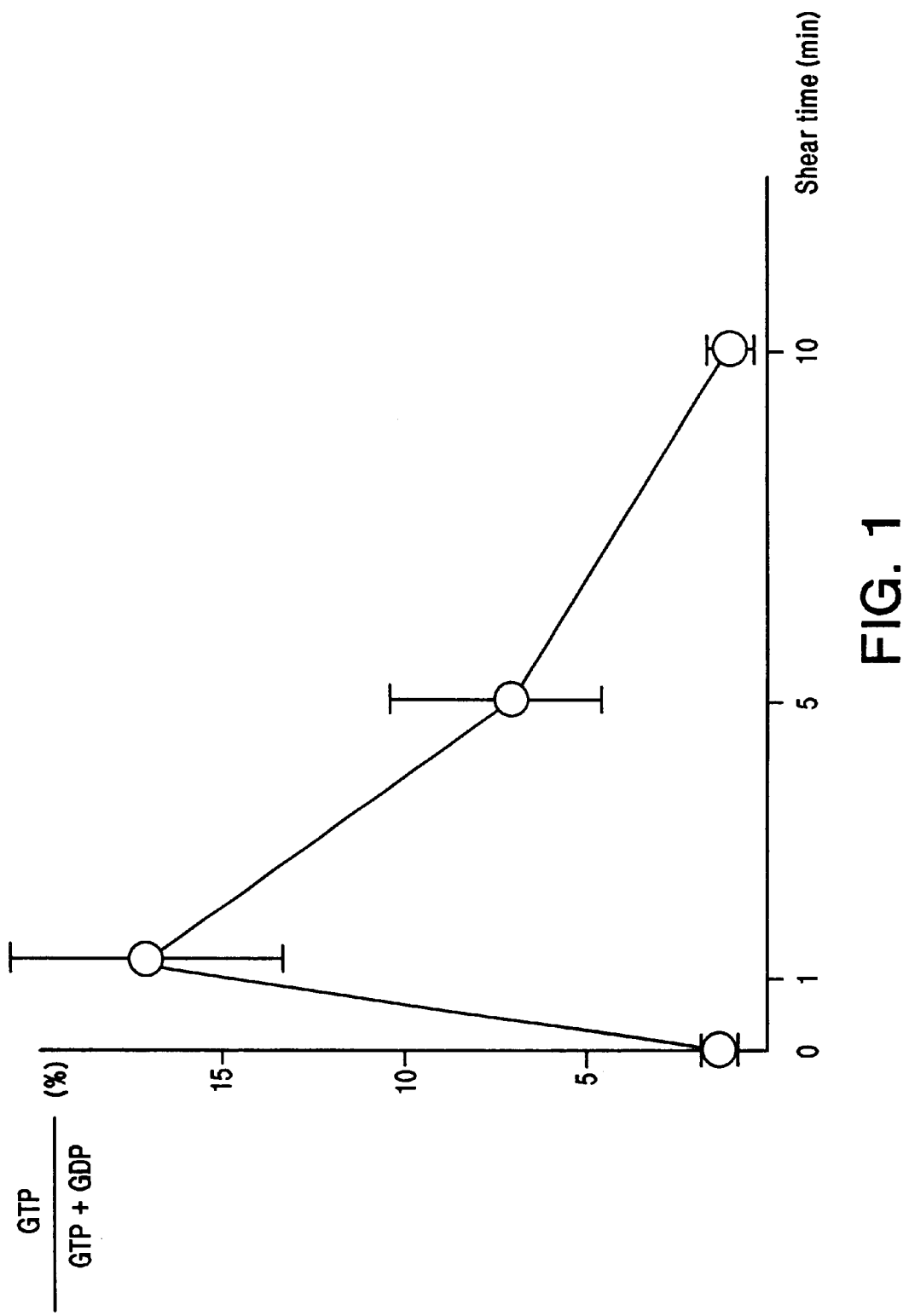
FIG. 1. Fluid shearing increases the ratio of $p21^{ras}$-GTP/$p21^{ras}$GDP. Monolayers of the $^{32}$P-labeled BAEC were either kept as static control (time 0) or subjected to a fluid shearing of 12 dynes/cm$^2$ for various periods of time as indicated. Guanine nucleotides were then eluted from the cell lysate and separated by TLC. The ratio of GTP/(GTP+GDP) was determined by densitometry. The results represent the mean ±SD from three studies.

Following long-standing patent law convention, the terms "a" and "an" mean "one or more" when used in this application, including the claims.

Several of the above sequences and sequences employed throughout the present specification include reference to particular amino acids. As will be recognized by those of skill in the art, each of the amino acids may be encoded by several different nucleic acid triplet codons. These various nucleic acid triplet codons are noted in Table 2. In some of the nucleic acid sequences, the designation "N" is used, and is intended to include a number of different nucleotides that encode a designated group or particular amino acid. The table 2 identifies the several different nucleotide triplet codons that encode a particular amino acid, and may be used in the selection of particular nucleic acid sequences encoding for an identified amino acid within the various nucleic acid sequences in the present disclosure.

TABLE 2

CODONS & ASSIGNED AMINO ACIDS

| First Position (5') | Second Position | | | | Third Position (3') |
|---|---|---|---|---|---|
| | U | C | A | G | |
| U | Phe | Ser | Tyr | Cys | U |
| | Phe | Ser | Tyr | Cys | C |
| | Phe | Ser | Ter* | Cys | A |
| | Phe | Ser | Ter* | Cys | G |
| C | Leu | Pro | His | Arg | U |
| | Leu | Pro | His | Arg | C |
| | Leu | Pro | His | Arg | A |
| | Leu | Pro | His | Arg | G |
| A | Ile | Thr | Asn | Ser | U |
| | Ile | Thr | Asn | Ser | C |
| | Ile | Thr | Asn | Ser | A |
| | Ile | Thr | Asn | Ser | G |
| G | Val | Ala | Asp | Gly | U |
| | Val | Ala | Asp | Gly | C |
| | Val | Ala | Asp | Gly | A |
| | Val** | Ala | Asp | Gly | G |

*Chain terminating
**Codes for Met if in the initiator position

Nucleic Acid Molecules

The invention also provides nucleic acid molecules of the substitution proteins and peptides, and their precursor molecules. In some embodiments, the nucleic acid molecules comprise at least a 10 or 20 nucleotide segment of defined nucleic acid sequences, such as the complement of those set forth at SEQ ID NO: 2, the molecule being capable of hybridizing to the nucleic acid sequence at SEQ ID NO: 2 under hybridization stringency conditions standard for hybridization fidelity and stability. These respective molecules may be further defined as comprising a nucleic acid sequence substantially free of nucleic acid sequences that do not encode a protein or peptide that competes with native Ras for biological activities of the native Ras.

In other embodiments, the nucleic molecules of the invention are defined as having a sequence comprising at least a 10, 20, 25, 30, 40, 50, 60, 70, 75, 80, 90, 100, 140, 150, 160, 40, 450, 480, 500 or 510 nucleotide segment of a substituted Ras peptide, such as that defined by the N-terminal fragment of substituted sequence for RAS at SEQ ID NO: 2. This molecule is further defined as being capable of hybridizing to the complementary sequence of the nucleic acid sequence of SEQ ID NO: 2 under relatively stringent hybridization conditions standard for hybridization fidelity and stability. The cDNA encoding a substitution mutant of Ras peptide having a substituted amino acid residue at position 17 is a further embodiment of the invention.

The isolated DNA molecules of the invention also may be described as a molecule selected from the group consisting of: (a) cDNA encoding a biologically active substitution Ras protein having a nucleotide sequence derived from the coding region of the sequence at SEQ ID NO: 2, 8, 9, 10 or 11 a DNA capable of hybridizing to the complementary cDNA of (a) under moderate conditions of stringency and (c) a DNA which is degenerate as a result of the genetic code to the DNA defined in (a) or (b) and which encodes a biologically active substitution mutant thereof capable of binding to or complementary binding with Ras.

In another embodiment, an isolated DNA molecule consisting essentially of a nucleotide sequence selected from the group consisting of a nucleotide sequence which encodes an antigenic fragment of said substituted Ras protein that includes the substituted amino acid, and a nucleotide sequence which hybridizes to the nucleotide sequence encoding said mutant, is provided.

In still other embodiments, the invention concerns isolated DNA segments and recombinant vectors that encode a protein or biologically active peptide fragment thereof that includes with its amino acid sequence an amino acid sequence essentially as set forth in SEQ ID NO: 4. Such references are also made in relation to the description of particular nucleotide sequences, such as those of SEQ ID NO: 8. The term "a sequence essentially set forth in SEQ ID NO:" means that the sequence substantially corresponds to a portion of the identified SEQ ID NO:, whether it be referencing an amino acid or nucleic acid sequence identifier, and has relatively few amino acids or nucleotide bases, as the case may be, which are not identical to, or biologically functional equivalent of, the amino acids or the nucleotides of the designated SEQ ID NO:

TABLE 1

Identification Of Sequences Having Sequence Identifiers

| SEQ ID NO: | DESCRIPTION |
|---|---|
| 1 | TGACTACA, TRE for the shear-induced reporter activities |
| 2 | Full Length Nucleic Acid Sequence (see FIG. 11), Positions 1–570 |
| 3 | Full Length Amino Acid Sequence (see FIG. 12), Positions 1–190 |
| 4 | Peptide, Amino Acid Positions 1–80 |
| 5 | Peptide, Amino Acid Positions 1–150 |
| 6 | Peptide, Amino Acid Positions 1–190 |
| 7 | Peptide, Amino Acid Positions 1–160 |
| 8 | Nucleic Acid Positions 1–240 |
| 9 | Nucleic Acid Positions 1–480 |
| 10 | Nucleic Acid Positions 1–450 |
| 11 | Nucleic Acid Positions 1–570 with the amino acid encoded by a triplet codon that encodes the amino acid at position 17, substituted with "N" |
| 12 | GCT; GCC; GCA; GCG; positions of substitution of #16 |
| 13 | GGT; GGC; GGA; GGG |
| 14 | AAG or AAA; |
| 15 | 5'-TTGTGGACGAATACGACC-3'; Primer sequence corresponding to the 5' end of the p21$^{ras}$ |
| 16 | CTACTCGAGCGTTACGAAGGTTACTTCTGCTCTAAAGCTC GGATCGATAAGCTTGCGCCAGGCCGGGGCCGAGCGATG ACGGAATATAAGCTGGTGGTGGTGGGCGCCGGCGGTGTT GGGCAAGAATGCGCT; partial sequence of the cloned RasN17 |
| 17 | MTEYKLVVVGAGGVGKNALTIQLIQ; amino acids 1–25, when amino acid 17 (designated by "X") is other than serine |

Materials and Methods

Cell Cultures and Fluid Shearing

Bovine aortic endothelial cells (BAEC) prior to passage 10 were used in all the studies. The cells were maintained in Dulbecco's modified Eagle's medium (DMEM) supplemented with 10% fetal bovine serum. All cell cultures were kept in a humidified 5% $CO_2$-95% air incubator at 37° C. BAEC were cultured on 38 mm×76 mm slides to confluence, and the slides were then assembled into a rectangular flow channel with a height of 270 µm, through which the medium flows. The system was tightly sealed by using a silicon gasket and a vacuum line. A surface area of 14 $cm^2$ on the BAEC-seeded slide, confined by the gasket, was exposed to the applied fluid shearing, which was generated by circulating the tissue culture medium through a hydrostatic pump connected to upper and lower reservoirs (15). The pH of the system was kept constant by gassing with 95%. air-5% $CO_2$, and the temperature was maintained at 37° C. by immersing the flow system in a water bath. The shear stress, determined by the flow rate perfusing the channel and the channel thickness, was 12 dynes/$cm^2$ (1 dyne=$10^{-5}$ Newton) which is relevant to the physiological range in the human major arteries and has been found to induce the expression of many IE genes in vitro (22, 40). The duration of the applied fluid shearing was 8 hr in the gene regulation experiments and varied from 1 to 60 min in the signal transduction experiments. Static control experiments were performed on BAEC on slides not exposed to fluid shearing.

P21$^{ras}$ Guanidine Nucleotide Binding Assay

The assays were performed according to the procedures described previously by Downward et al. (12) with minor modifications. BAEC cultured on a glass slide were labeled with 0.5 mCi/ml [$^{32}$P]orthophosphate (ICN Radiochemicals) for 6 hr in a phosphate-free medium. After labeling, the cells were subjected to fluid shearing or kept as static controls. Cell extracts were then prepared afterwards by lysing the BAEC in a buffer containing 50 mM Tris-HCl, pH 7.5, 0.5%-NP-40, 0.15 M NaCl, 0.1 mM $Na_3$ $VO_4$, 20 mM $MgCl_2$, 0.5% Trotpm X-100, 1 µg/ml leupeptin, 1 mM PMSF, 2 mM DTT, and 2 mM β-glycerolphosphate. Ras proteins were immunoprecipitated with rat anti-p21$^{ras}$ mAb (Santa Cruz). The bound guanine nucleotides were separated from the precipitated protein complexes by using a buffer containing 20 mM Tris-HCl, pH 7.5, 20 mM EDTA, 2 mM DTT, 2% SDS, and 2 mM GTP. The eluted nucleotides were separated by thin layer chromatography using PEI-cellulose plates with 0.75 M $K_2HPO_4$, pH 3.4. The GDP and GTP contents were assessed by autoradiography.

Assays of ERK and JNK Activities

Five micrograms of anti .MAPK/protein A-Agarose (UBS), in a buffer containing 20 mM HEPES (pH 7.7), 75 mM NaCl, 2.5 mM-$MgCl_2$, 0.1 mM EDTA, 0.05% Triton X-100, 0.5 mM DTT, 20 mM β-glycerolphosphate, 0.1 mM $Na_3$ $VO_4$, 2 µg/ml leupeptin, and 100 µg/ml PMSF, were added to the cell lysate to immunoprecipitate ERK. The suspension was mixed in 4° C. for 4 hr and centrifuged. The pelleted beads were washed in phosphate buffer saline containing 0.1% Triton X-100, followed by resuspension in 30 µl of a kinase buffer which contained 20 mM HEPES (pH 7.6), 20 mM $MgCl_2$ 20 mM β-glycerolphosphate, 20 mM p-nitrophenyl phosphate, 0.1 mM $N_3VO_4$, 2 mM DIT, 20 µM ATP, 5 µg myelin basic protein (MBP), and 5 µCi [$γ^{32}$P]ATP. After incubation at 30° C. for 20 min, the kinase reaction was terminated by washing with HEPES binding buffer. The phosphorylated proteins were eluted in 30 µl of 2×Laemelli sample buffer and resolved on 10% SDS-polyacrylamide gel, followed by autoradiography. The procedures for JNK activity assay were the same as for ERK, except that 1 µg agarose-bound glutathione-S-transferase (GST)-c-Jun(1-223) (19) and 5 µCi [$γ^{32}$P]ATP were added directly to the cell lysate for kinase reaction. In some of the experiments, plasmid encoding HA-JNK was transfected into BAEC and the exogenous epitope-tagged was immunoprecipitated with a mouse anti-HA mAb (Boehringer Mannheim). The following procedures to assay the activity of the JNK were the same as described above.

Plasmids

ERK(K52R) and ERK(K71R) were gifts from Dr. Melanie Cobb at University of Texas. HA-JNK, Ga14-c-Jun(1-223), Ga14-c-Jun(1-223, Ala63/73), MEKK(K-M), Raf301, RasNI7, mSOS1, and ∆mSOS1 were described previously (10, 14, 24, 32, 34, 39). To construct JNK(K-R), JNK 1 was mutated in pBluescript by PCR to introduce a NcoI site at its first ATG codon and a point mutation at codon 55 which replaced the Lys-55 with an Arg. The mutations were confirmed by DNA sequencing. The mutated JNK was then subcloned into expression vector SRα3HA (9) at NcoI and BgIII sites to create JNK(K-R).

AP-1/TRE Activation Assays

Expression plasmids encoding the wild-type, active, or dominant negative mutants of p21$^{ras}$, MEKK, or JNK were co-transfected with either 4×TRE-P1-Luc or MCP1-Luc-540 into BAEC at 70% confluence by using the transient transfection protocols. 4×TRE-P1-Luc is a construct in which the rat Ras promoter conjugated to luciferase reporter is driven by four copies of the TRE consensus sequence, and MCP1-Luc-540 is a construct in which the luciferase reporter is driven by the 540-bp MCP-1 promoter (41). The pSV-β-galactosidase plasmid, which contains a β-galactosidase (β gal) gene driven by SV40 promoter and enhancer, was also included in the co-transfection to monitor the transfection efficiency. After incubation for 6 hr, the cells were washed with PBS and incubated with fresh media for another 24–48 hr to reach confluence. The cells in the tissue culture flasks were then seeded on glass slides and used either for fluid shearing experiments or as static controls. The luciferase reporter activities of the various experiments normalized for transfection efficiency were used to assess the suppressing effects of the various negative mutants on the shear-induced transcription activation mediated by AP-1/TRE.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

$p21^{ras}$ is Activated by Fluid Shearing in BAEC

To investigate whether fluid shearing leads to an activation of $p21^{ras}$ in ECs, i.e., an increased ratio of $p21^{ras}$ GTP to $p21^{ras}$ GDP, confluent monolayers of the $^{32}$P-labeled BAEC were subjected to a fluid shearing of 12 dynes/cm$^2$ for various time periods, and the cells were lysed and subjected to guanine nucleotide binding assays. In the static controls, $p21^{ras}$ was exclusively in its GDP-bound inactive form (FIG. 1). After shearing for 1 min., the ratio of $p21^{ras}$ GTP/$p21^{ras}$ GDP increased markedly. Densitometric analysis indicated that 17±4% of all the guanine nucleotides bound to $p21^{ras}$ was GTP bound. This GTP-bound active from gradually returned to the GDP-bound form afterwards. By 5 min after the beginning of shearing, the GTP bound form decreased to 7±3%. By 10 min, all $p21^{ras}$ became inactive, as in the static controls. Thus, fluid shearing, like other extracellular stimuli such as mitogens, cytokines, osmotic shock, and UV irradiation, induces a transient activation of $p21^{ras}$.

EXAMPLE 2

The Shear-Activated AP-1/TRE is Mediated Through $p21^{ras}$

Figure 2B:
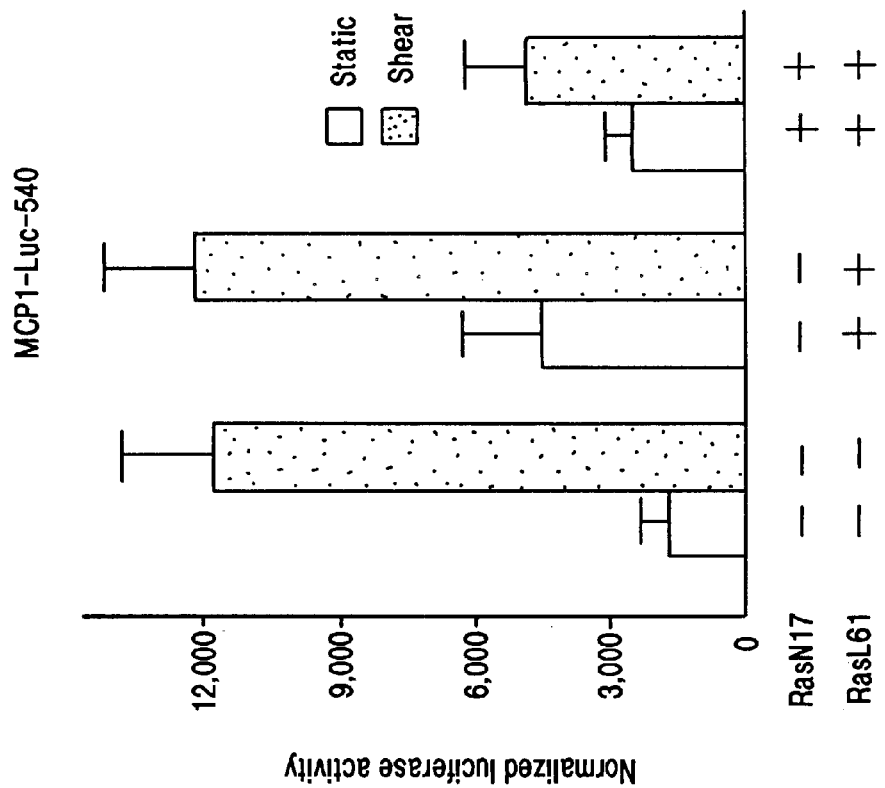
FIGS. 2A and 2B. RasN17 abolished the shear-induced AP-1/TRE activation. pcDNA3 empty vector, expression plasmid encoding RasL61, or RasNI7 was co-transfected with 4×TRE-P1-Luc (A), or MCP1-Luc-540 (B) into BAEC in a tissue culture flask. The DNA-trarsfected cells were re-seeded on culture slides until confluence and either subjected to a fluid shearing of 12 dynes/cm$^2$ for 8 hr (dark bars) or kept as static control (open bars) followed by luciferase activities assays. The normalized luciferase activities are the luminometer readings of luciferase activity normalized for transfection efficiency based on β-galactosidase activity. The results represent the mean ±SD from at least three studies.
Figure 2A:
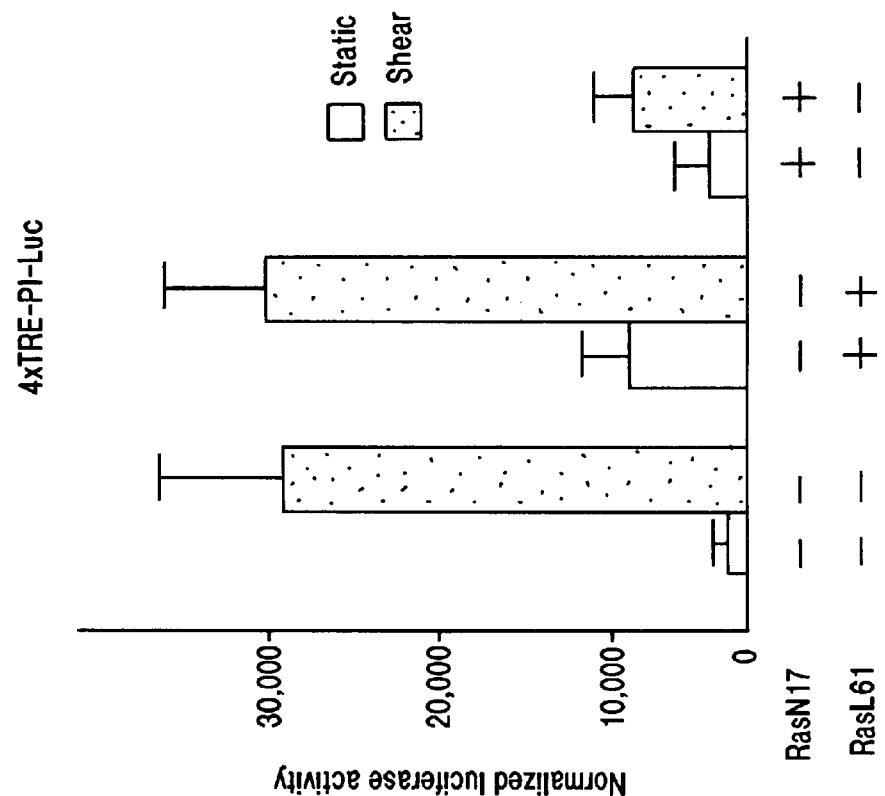

By using transient transfection assays, the present inventors show that the luciferase reporter driven by TRE (i.e., 4×TRE-P1-Luc and MCP1-Luc-540) can be induced by fluid shearing. Transactivation asssays using c-Jun or c-Jun/c-Fos expression plasmids also induced these TRE-driven constructs (41), indicating that the transcription factor that mediates such activation is AP-1. To investigate whether the Ras is upstream to the shear-induced activation of AP-1/TRE, we examined the effects of RasN17 on the induction of 4×TRE-P1-Luc and MCPI-Luc-540. RasN17 is a dominant negative mutant of Ras in which Ser-17 in the wild-type has been replaced by Asn, so that the affinity to GTP is dramatically reduced (14). As shown in FIG. 2, in the plasmid control experiments, fluid shearing caused 23 and 6.5 folds of induction (the luciferase activates in the sheared cells compared to those in the static controls) for 4×TRE-P1-Luc and MCPI-Luc-540, respectively. The present inventors also transfected expression plasmid encoding RasL61, the active form of $p21^{ras}$ in which the Gln-61 in the wild-type has been replaced by Leu, into BAEC. The expression of RasL61 increased the basal level expression for both 4×TRE-P1-Luc and MCPI-Luc-540. However, the induction by fluid shearing was not affected. In contrast, the co-transfection of RasN17 with either 4×TRE-P1-Luc or MCPI-Luc-40 into BAEC significantly decreased the shear-induced luciferase reporter activities. These results, together with those presented in FIG. 1, suggest that a functional $p21^{ras}$ is required for the AP-1/TRE-mediated gene expression in response to fluid shearing.

EXAMPLE 3

Fluid Shearing Acticates JNK to a Greater Extent than ERK

Figure 3A:
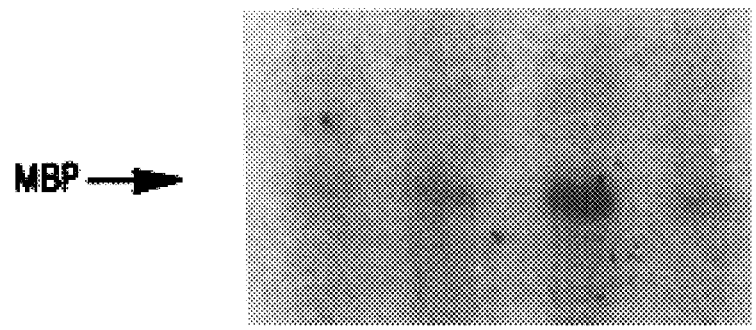
FIGS. 3A and 3B. Fluid shearing preferentially activates JNK. BAEC were subjected to fluid shearing of 12 dynes/cm$^2$ for various lengths of time, as indicated. In (3A), after shearing, ERK was immunoprecipitated and the kinase activity assay was performed in the presence of myelin basic protein (MBP) and ($\gamma$-$^{32}$P)ATP. In (3B), the cell lysate was incubated with agarose-bound GST-c-Jun to precipitate JNK followed by the addition of ($\gamma$-$^{32}$P)ATP. Static controls are represented by time 0, and the 20- and 39-Kd phosphorylated MBP and GST-c-Jun are indicated by arrows. Densitometric analysis indicated that the peak fold of induction (compared to the static control) was 1.8×at 10 min in (3A), and 10.5×at 30 min in (3B).

In ECs, ERK-1 and -2 are shown to be phosphorylated by fluid shearing (41). To investigate whether the phosphorylation of ERK led to their increased kinase activities, BAEC were subjected to shearing at 12 dynes/cm$^2$ for various lengths of time. As shown in FIG. 3A, such a mechanical stimulation induced a rapid activation of ERK to cause MBP phosphorylation, which peaked at 10 min and decreased afterwards. Densitometric analysis indicated that the peak activity was 1.8 folds of that in the static controls. To investigate whether fluid shearing activates JNK as it does for ERK, agarose-bound GST-c-Jun, a fusion protein containing GST and the N-terminal moiety (1-223) of c-Jun, and [γ-$^{32}$P]ATP were added to the cell lysate for JNK in BAEC to cause c-Jun phosphorylation, which peaked at 30 min and decreased afterwards. After the cells had been exposed to the shearing for 60 min, the JNK activities returned to a level lower than that in the static controls. The JNK activity peaked, at 30 min and decreased afterwards. After the cells had been exposed to the shearing for 60 min, the JNK activities returned to a level lower than that in the static controls. The peak JNK activity, at 30 min, determined by densitometry, was 10.5 folds of that in the static cells. Kinase assays on static cells incubated with fresh media or with conditioned media collected from sheared cells showed no difference in kinase activities from the static controls (data not shown). These results indicate that the activation of cytoplasmic kinases in the sheared cells was attributable to the action of mechanical force rather than by the media supplements or by the metabolites released from the cells during shearing. Furthermore, fluid shearing of BAEC activates JNK to a greater extent and for a longer duration than ERK.

EXAMPLE 4

$p21^{ras}$ and MEKK are Upstream to the Shear-Activated JNK

Figure 4A:
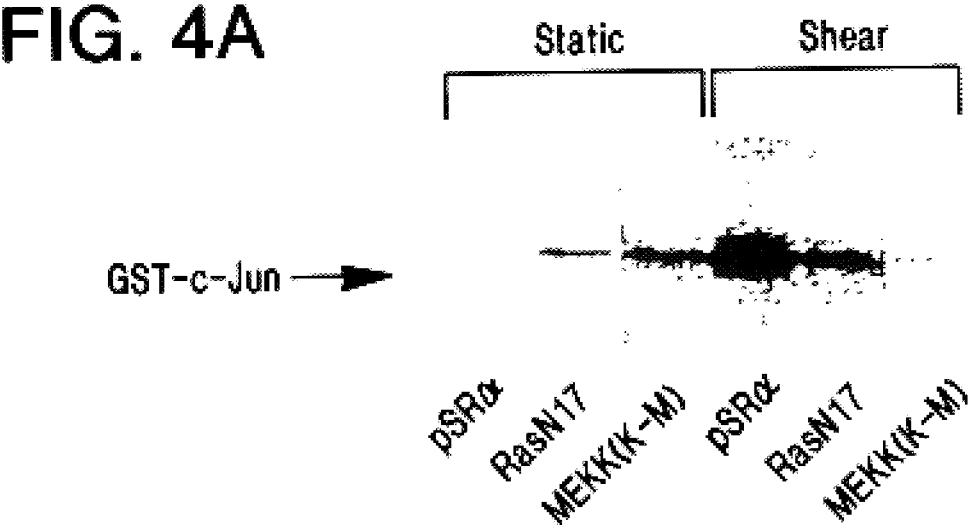
FIGS. 4A and 4B. P21$^{ras}$ and MEKK are upstream to the shear-activated JNK. Ten micrograms of expression plasmid encoding HA-JNK was co-transfected with either 10 $\mu$g SRα empty plasmids, RasNI7, or MEKK(K-M) into BAEC in a T-75 tissue culture flask. The transfected cells on culture slides were either kept as static controls (Static) or subjected to a fluid shearing of 12 dynes/cm$^2$ for 30 min (Shear). After shearing, HA-JNK was immunoprecipitated with anti-HA mAb and subjected to kinase assays using GST-c-Jun and [$\gamma$-$^{32}$P]ATP as substrates (4A). The phosphorylated GST-c-Jun is indicated by arrow. RasNI7 and MEKK(K-M) inhibited the shear-induced phosphorylation of GST-c-Jun. Shown in (4B) is the immuno blotting of the cellular proteins with anti-HA mAb. The equal intensities of the bands recognized by ECL detection reagents indicate that the amounts of the expressed HA-JNK were the same in different samples.
Figure 4B:
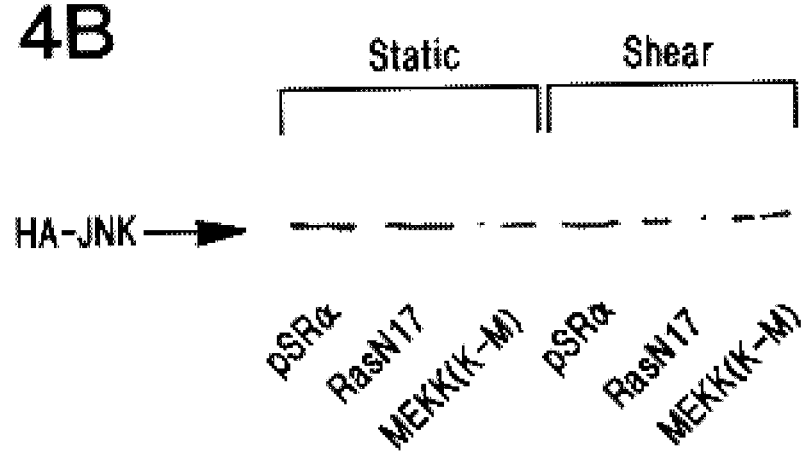

Whether $p21^{ras}$ is upstream to such shear-activated JNK was further investigated. Kinase assays shown in FIG. 4 indicate that the exogenous epitope-tagged HA-JNK was also activated by fluid shearing in the transfected BAEC. The co-transfection of RasN17 inhibited such shear-induced kinase activity of HA-JNK as manifested by the phosphorylation of its substrate GST-C-Jun (FIG. 4A). It has been shown that the expression of Ras activates MEKK (27) and that the induction of MEKK stimulates JNK (48). Co-transfection of a catalytically inactive enzyme MEKK (K-M), in which the Lys-432 had been replaced by a Met (32), with HA-JNK also reduced the shear-induced JNK activity (FIG. 4A). These results indicate that fluid shearing activates a Ras-MEKK-JNK pathway in the vascular EC's.

EXAMPLE 5

Negative Mutants of MEKK and JNK Block the Shear-Activated AP-1/TRE

Figures 5A, 5B:
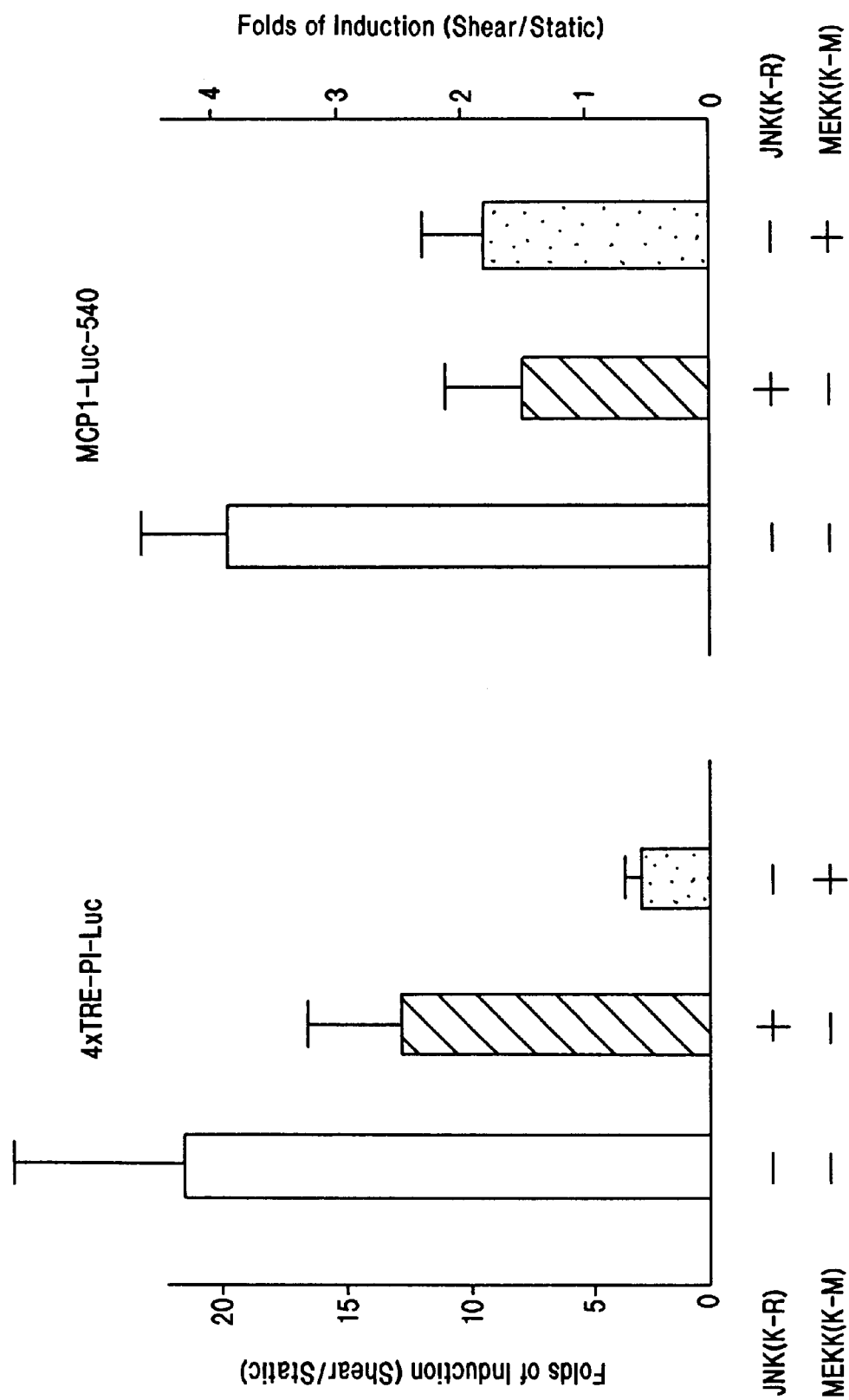
FIGS. 5A and 5B. JNK(K-R) and MEKK(K-M) attenuate the shear-induced AP-1/TRE activation. Expression plasmids encoding JNK(K-R) or MEKK(K-M) were co-transfected with 4×TRE-P1-Luc (A), or with MCP1-Luc-540 (B) into BAEC. The experimental conditions were the same as those described in FIG. 2. The folds of induction were the normalized luciferase activities in the experimental cells compared to those in static controls. The results represent the mean±SD from six experiments.

To further examine whether MEKK mediates the shear-induced reporter driven by AP-1/TRE, co-transfection of MEKK (K-M) with either 4×TRE-P1-Luc-540 was done. In addition, JNK (K-R), a kinase deficient JNK1, in which the Lys-52 in the wild-type was replaced by an Arg, was constructed. If the Ras-MEKK-JNK pathway is upstream to the AP-1/TRE, the use of either MEKK(K-M) or JNK(K-R) to block the functions of the wild-types should attenuate the shear-induced AP-1/TRE. FIG. 5A indicates that the co-transfection of expression plasmids encoding MEKK(K-M) or JNK)K-R) did attenuate the shear-induced 4×TRE-P1-Luc from 21.5 folds to 12.5 or 4 folds, respectively. Co-transfection of these catalytically inactive mutants with MCPI-Luc-540 also reduced the shear induced luciferase reporter activities (FIG. 5B). In contrast, co-transfection of the expression plasmids encoding the wild-type MEKK or JNK did not affect the shear-induced 4×TRE-P1-Luc or MCPI-Luc-540. Thus, MEKK and JNK are upstream to the AP-1/TRE mediated gene expression in response to shear stress.

EXAMPLE 6

Figure 3B:
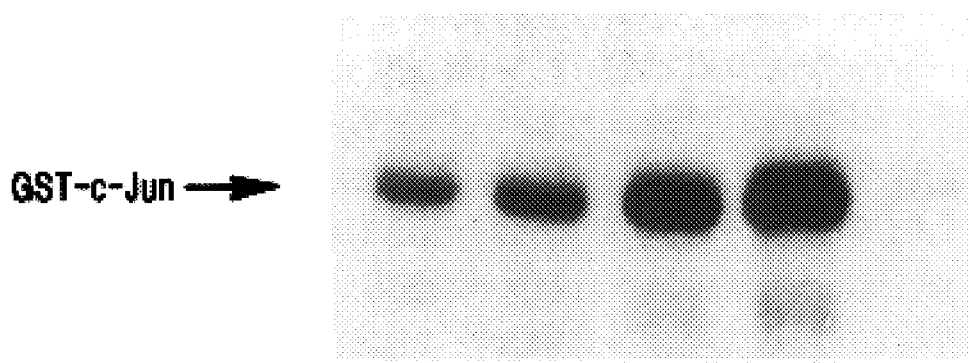
Figure 6:
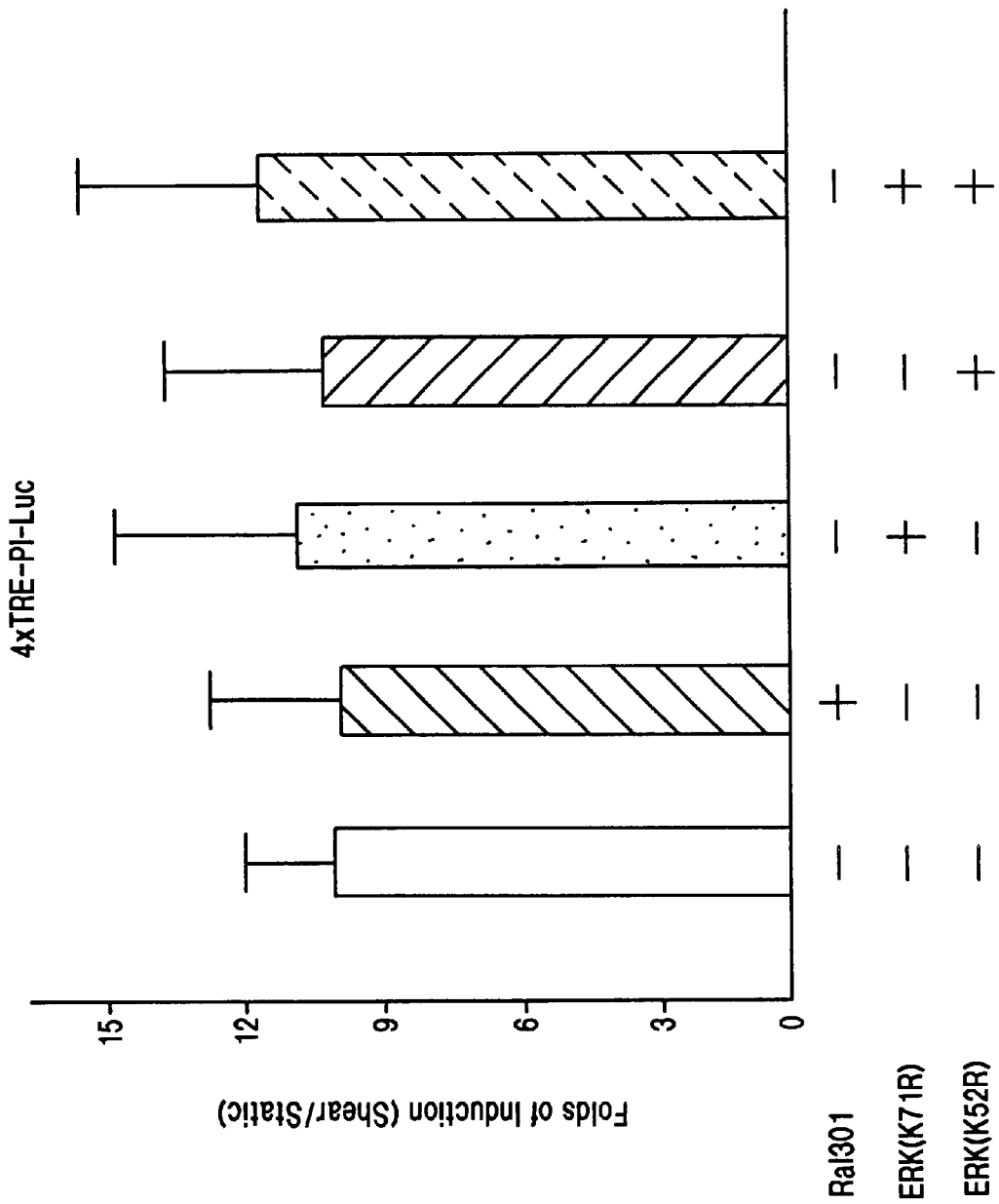
FIG. 6. Raf-1 and ERK are not required for the shear-induced AP-1/TRE. Chimeric construct 4×TRE-P1-Luc was transiently transfected alone or with other plasmids encoding the various dominant negative mutants into BAEC for fluid shearing/luciferase assays. The experimental conditions were the same as those in FIG. 2. The folds of induction were the normalized luciferase activities in the experimental cells compared to those in static controls. The results represent the mean±SD from six experiments.

RAF-301, ERK(52R), and ERK(71r) have Little Effects on the Shear-Activated AP-1/TRE In response to the stimulations by growth factors or phorbol ester, the Ras-ERK pathway is activated (11, 46), leading to the activation of AP-1/TRE (16). Raf-1contributes directly to ERK activation in this pathway, but not to JNK activation (23). Mechanical shearing has a less potent effect on ERK than on JNK (FIG. 3), which seams to indicate that the Ras-Raf-1-ERK pathway is less important for the downstream gene expression. To test the role played by he Ras-Raf-1-ERK pathway in the shear-induced activation of AP-1/TRE, we used the dominant negative mutants of Raf-1 and ERK to block this pathway and examined the AP-1/TRE-mediated reporter activities in response to mechanical stimulation. Raf301 is a dominant negative mutant of Raf-1 in which the Lys-375 in the wild-type has been replaced by Trp (24). ERK(K71R) and ERK(K52R) are the dominant mutants of ERK1 and ERK2, in which the respective Lys71 and Lys-52 in the wild types as been replaced by Arg (36). FIG. 6 shows that co-transfection of Ra301 had little effect on the shear-induced 4×TRE-P1-Luc reporter activity. Similarly, neither ERK(71R), ERK(52r), nor a combination of these two ERK dominant negative mutants attenuated the reporter activity in response to fluid shearing. Experiments using MCP1-Luc-540 also showed that none of these negative mutants was able to affect the shear-induced luciferase activity (data not shown). Thus, the Ras-Raf-1-ERK pathway is not essential for the shear-induced activation of AP-1/TRE.

EXAMPLE 7

Fluid Shearing Increases c-Jun Transcriptional Activity

It seems that the induction of 4×TRE-P1-Luc and MCPI-Luc-540 by fluid shearing results from an up-regulated c-Jun, which is activated by the Ras-MEKK-JNK pathway To test whether fluid shearing increases the transcriptional activity of c-Jun, plasmid Ga14-C-Jun encoding the fusion protein of Ga14 DNA binding domain and c-Jun activation domain (1-223) were co-transfected with 4×Ga1-Luc, a chimeric construct consisting of he Ga14-binding sequence and the luciferase reporter, into BAEC. Compared to the static controls, fluid shearing increased the luciferase activity by more than 4 folds in the sheared cells (FIG. 7), indicating an increased c-Jun transcriptional activity. In contrast, the plasmid encoding the mutated Ga14-Jun, in which the phosphorylation sites Ser-63 and -73 had been replaced by Ala, showed a marked reduction in response to fluid shearing. Furthermore, co-expression of RasN17 or MEKK (K-M) also attenuated such shear-induced transcriptional activity. Thus, the fluid-shearing induced activation of AP-1 is at least in part due to an increased c-Jun transcriptional activity, which is in turn activated through the phosphorylation of Ser-63 and -73 by the Ras-MEKK-JNK pathway.

EXAMPLE 8

ΔmSOS1 Attenuates the Shear-Induced c-Jun Transcriptional Activity

Figures 7A, 7B:
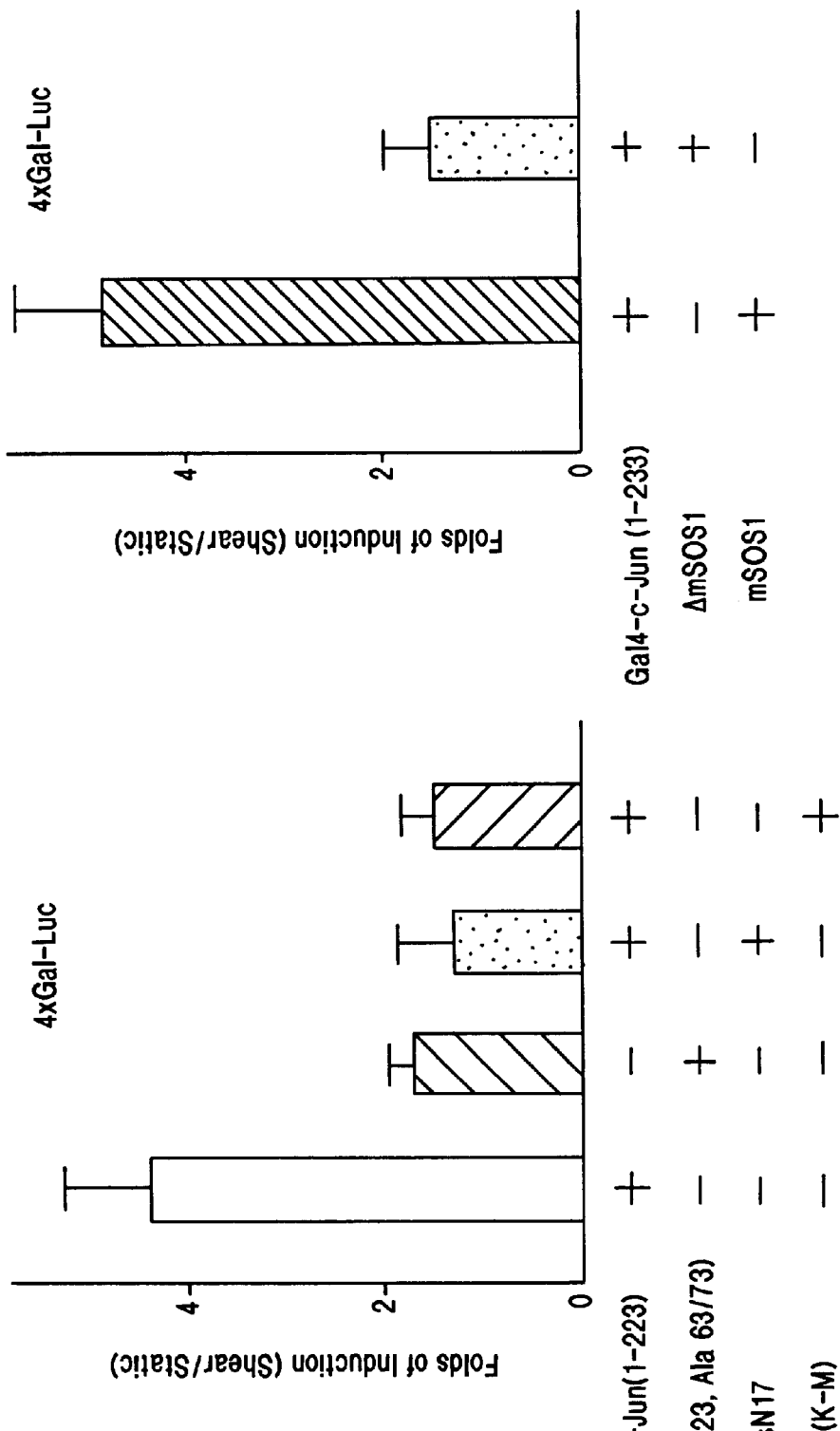
FIGS. 7A and 7B. Fluid shearing increases the transcriptional activity of c-Jun and appropriate mutants attenuate this shear-induced activity. In (A), BAEC were transfected with 6 $\mu$g 4×Gal-Luc, 6 $\mu$g Gal4-c-Jun (1-223), 6 $\mu$g Gal4-c-Jun (1-223, Ala63/73), 18 $\mu$g RasNI7, or 18 $\mu$g MEKK(K-M), as indicated. In (B), BAEC were transfected with same amounts of 4×Gal-Luc and Gal4-c-Jun(1-223), together with either 18 $\mu$g mSOS1 or 18 $\mu$g ΔmSOS1. The experimental conditions were the same as those described in FIG. 2. The folds of induction were the normalized luciferase activities in the experimental cells compared to those in static controls. The results represent the mean±SD from six experiments.
Figure 8:
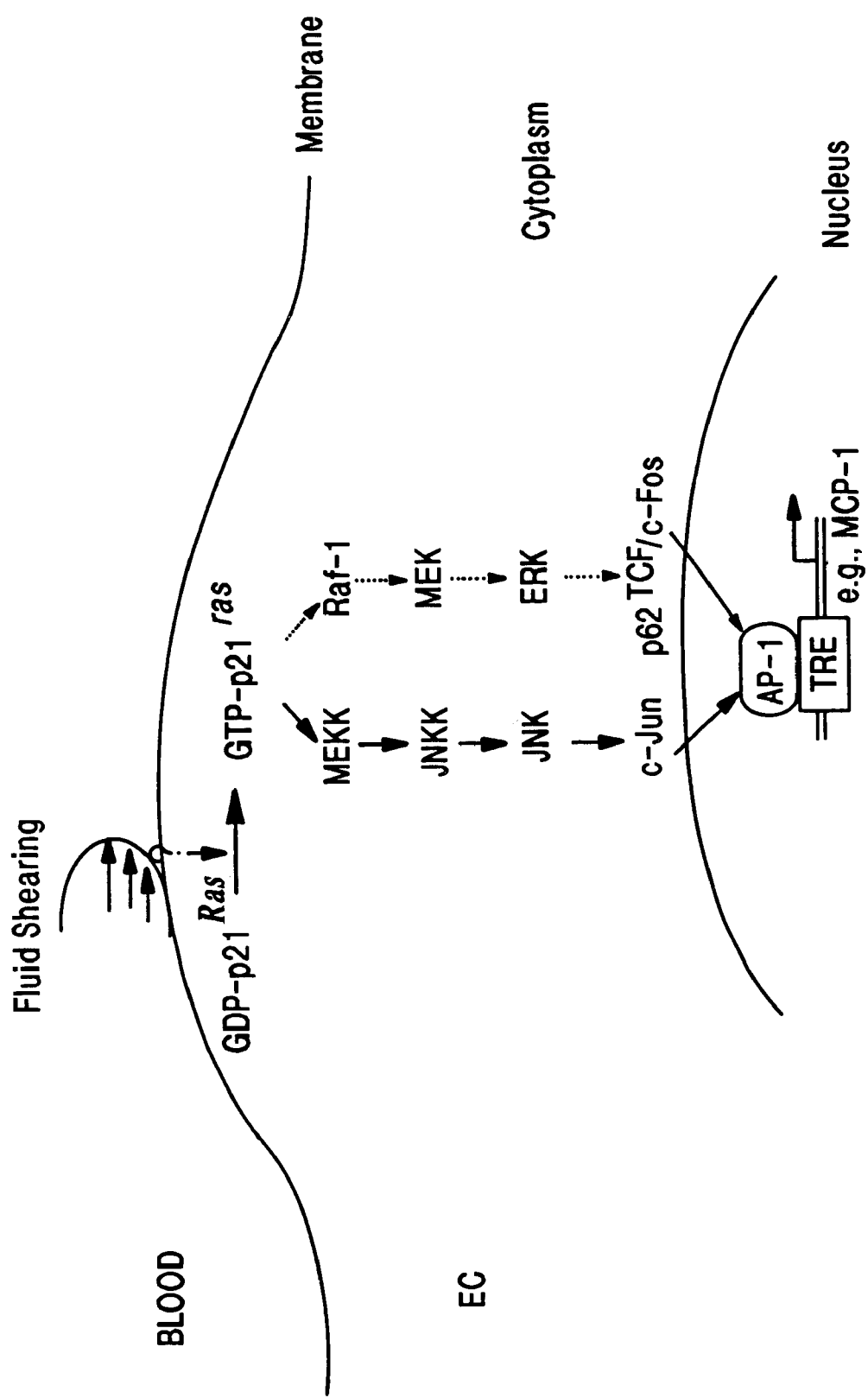
FIG. 8. The fluid shearing-elicited signal transduction pathways leading to the AP-1/TRE-mediated gene expression (as exemplified by the MCP-1 gene) in ECs. The mechano-biochemical transduction most likely occurs on the membrane by undefined sensors/receptors that activate the membrane-associated p21$^{ras}$. Subsequently, the MEKK-JNKK-JNK pathway is activated preferentially. As a result, c-Jun is phosphorylated to increase its transcnptional activity and the Jun-Jun homodimer activates the TRE-containers. The Raf-MEK-ERK pathway, although also activated by the hemodynamic force, is much less important and probably not necessary for the activation of AP-1I/TRE.

Son of sevenless (Sos) is a guanine nucleotide exchange factor that activates $p21^{ras}$ by converting the GDP-bound inactive state to the GTP-bound active state (4, 13). To explore whether Sos is a upstream molecule regulating the shear-activated Ras signaling, expression plasmids encoding ΔmSOS1, a dominant negative mutant of muse SOS1 in which the guanine nucleotide exchange domain has been deleted (39), were co-transfected with Ga14-c-Jun and 4×Gal-Luc into BAEC. The transfected cells were then subjected to fluid shearing/luciferase assays. As shown in FIG. 7B, ΔmSOS1 attenuated the shear-induced c-Jun transcriptional activity. The inducibiliy by fluid shearing in cells transfected with mSOS1, the wild-type mouse SOS1, was comparable to that in cells transfected with empty vectors.

EXAMPLE 9

Construction of Recombinant Ad-RasN17

A recombinant adenovirus, AdRasN17, was constructed by cotransfecting 293 embryonic kidney cell line with pACCMVpLpA (8.8 Kb), a shuttle vector containing RasN17 cDNA, and pJM17, a vector carrying a dl309 adenovirus 5 genome (Ad5). After the homologous recombination between pACCMBpLpA and pJM17 in 293 cells, the adenovirus E1 region responsible for viral replication was substituted by RasN17 expression cassette, resulting in replication-deficient viruses. Southern blot assay was performed to identify the viruses containing the RasN17 DNA. The of this preparation was determined by optical density measurement.

EXAMPLE 10

RasN17 Inhibits the AP-1/Tre-Mediated Transactivation in Response to Serum or PDGF The cloned RasN17 adenovirus shuttle vector and a luciferase reporter driven by TPA-responsive elements (4×TRE-PL-Luc) were co-transfected into bovine aortic endothelial cells (BAEC). The transfected cells in serum-free medium were treated with either 15% serum or 10 ng/ml PDGF for 24 hr, and this was followed by luciferase activity assays. FIG. 2 shows that the induction of luciferase activity by serum or PDGF in the control cells is significantly attenuated by the co-transfection of RasN17. These results indicate that the AP-1/TRE-mediated gene expression (e.g., MCP-1) induced by mitogenic stimuli in vascular endothelium can be blocked by RasN 17.

EXAMPLE 11

Constructing and Confirming the RasN17 cDNA Sequence

Construction of Recombinant Adenoviruses

A recombinant adenovirus, AdRasN17, was assembled by transfecting 293 embryonic kidney cell line with pACCM-$V_pL_pA$ (8.8 Kb), a shuttle vector containing RasN17 cDNA, and pJM17, a vector carrying a dl309 adenovirus 5 genome (Ad5). The pJM17 contains the full length Ad5 genome (36 kb) with the interruption of a 4.3 kb unrelated DNA fragment at position 3.7 map units, thereby exceeding the adenoviral packaging limit. After the homologous recombination between pACCMB$_p$L$_p$A and pJM17 in 293 cells, the adenovirus E1 region responsible for viral replication was substituted by the RasN17 expression cassette, resulting in replication-deficient viruses. Putative viral clone were plaque purified, propagated, isolated, and the tier was determined according to the established procedures. Southern blot was performed to verify the insertion of RasN17 DNA into viruses. The control adenoviral vector containing a LacZ gene expression cassette (AdLacZ) was constructed by similar procedures. AdLacZ was obtained from 293 cells co-transfected with pJM17 and pXCJL 1/CMV/n1s-LacZ, a derivative of pXCJL.1 that carries an expression cassette in which the human cytomegalovirus IE promoter encoding the SV40 large T-antigen nuclear-localization signal was fused to the *E.coli* LacZ reporter gene.

Confirming the RasN17 cDNA Sequence

A primer with sequence 5'-TTGTGGACGAATACGACC-3' corresponding to the 5' end of p21ras cDNA was used to sequence the RasN17 (SEQ ID NO:16) cloned into the adenoviral vector pJM17. The partial sequence of the cloned RasN17 is as follows:

EXAMPLE 13

Cocktail of RasN17 and Other Molecules in Ras Pathways

An adenovirus-based system to deliver the negative mutants in the Ras-mediated signaling pathway to vascular cells was developed. These molecules, which include, but are not limited to, negative mutants of Son of Sevenless (Sos), MEKK, JNKK, JNK, Raf and ERK, have been previously shown to attenuate the downstream gene expression. This development is aiming at blocking the Ras pathway in a comprehensive manner so that the expression of genes involved in atherogenesis and restenosis can be effectively abolished.

EXAMPLE 14

RasN17 Inhibits the Induction of Ap-1/Tre by Serum or PDGF in Endothelial Cells The cloned RasN17 adenovirus shuttle vector and a luciferase reporter driven by TPA-responsive elements (4×TRE-P1-Luc) were co-transfected into bovine aortic endothelial cells (BAEC). Each group of cells were cultured in serum-free medium for 24 hours followed by addition of ether 15% serum or 10 ng/ml platelet derived growth factor (PDGF) for another 24 hour incubation, followed by luciferase activity assays. FIG. 2 shows that the induction of luciferase activity by serum or PDGF in the control cells is significantly attenuated by the co-transfection of RasN17. These results indicate that the Ap-1TRE-mediated gene expression (e.g., MCP-1) induced by mitogenic stimuli in vascular endothelium can be blocked by RasN17.

EXAMPLE 15

Use of RasN17 to Attenuate Vascular Smooth Muscle Proliferation In vitro

The present example is provided because the proliferate response of VSMC to high-serum or PDGF culture conditions in vitro resembles heir hyperplastic response to balloon

```
CTACTCGAGCGTTACGAAGGTTACTTCTGCTCTAAAGCTCGGATCGATAAGCTTGGG

CCAGGCCGGGGCCGAGCGATGACGGAATATAAGCTGGTGGTGGTGGGCGCCGGCGG
            cloning site TGTTGGGCAAGAATGCGCT
        Ser→Asn
```

EXAMPLE 12

Ad-RasN17 Inhibits the Serum and PDGF-Induced Mitotic Responses in Pig Smooth Muscle Cells By introducing a reporter gene LacZ, it was found that the transfection efficiency of DNA into porcine smooth muscle cells by liposome is poor. Only approximately 5% of cells can be transfected, as demonstrated by X-Gal staining in FIG. 13A. In order to test DNA transfection efficiency mediated by adenovirus, an adenovirus containing LacZ gene, Ad-LacZ, was used to determine the transfection efficiency. As shown in FIG. 13B, the majority of the smooth muscle cells (>95%) are X-Gal staining positive, indicating the successful injection of these cells by Ad-LacZ. Thus, adenoviral vector is superior to liposomes as a delivery system to transfer therapeutic genes into vascular cells.

injury in vivo. 15% serum or 10 ng/ml PDGF was applied to the serum starved porcine VSMC after transfection with a replication-deficient virus carrying the RasN17 gene (Ad-RasN17). In controls, replication-deficient virus carrying the LacZ gene (Ad-LacZ) was used. The $^3$H-Thymidine incorporation assay was performed to assess cell proliferation. In vitro, VSMC stimulated with serum and PDGF showed proliferate response in the Ad-LacZ control group, but this was inhibited in the Ad-RasN17 transfected group.

Adenovirus-mediated Transfection and $^3$H-Thymidine Incorporation Assays

PSMCs were seeded on 96-well plates until 50% confluence. The cells were then infected with the replication-deficient adenovirus AdlacZ or AdRasN17 in $1\times10^6$, $1\times10^7$, or $1\times10^8$ plaque-forming units per milliliter (pfu/ml). After 24-hr infection, the infected cells were starved in DMEM containing 0.5% serum for 24 hr followed by stimulation with 15% serum or 10 ng/ml PDGF. The cells were pulse-labeled for 4 hr in growth media containing 2.5 µC/ml methyl-$^3$H thymidine (Amersham Life Science). The cells were trypsinized and collected on glass fiber filter papers. The filter papers were collected in polypropylene vials, mixed with 5 ml scintillate per sample for 12 hr, and counted in a beta scintillation counter.

RasN17 Inhibits the Proliferation of PSMCs in Response to Mitogens

Figure 9A:
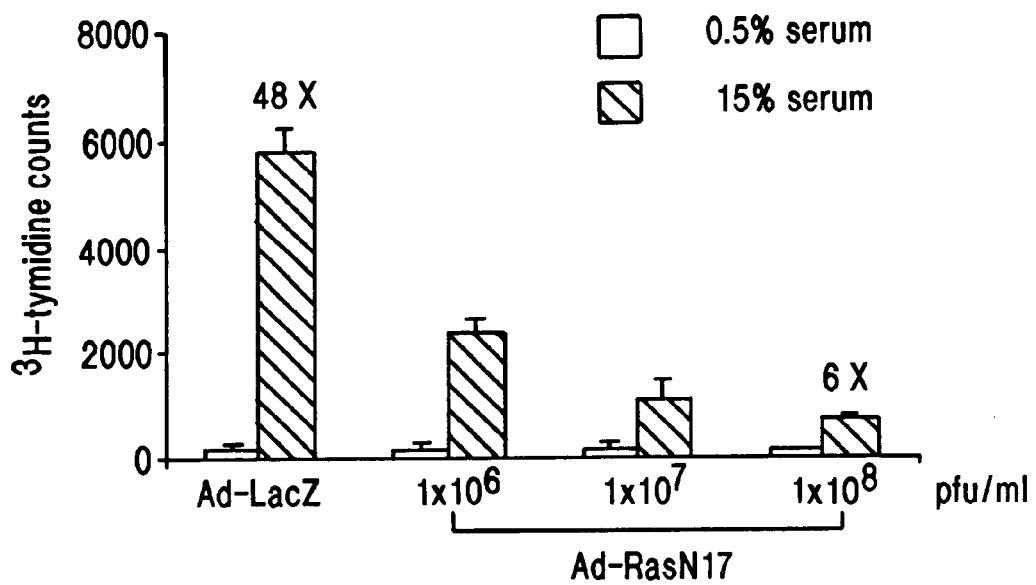
FIGS. 9A and 9B. Ad-RasN17 attenuates the mitotic responses of PSMCs to Serum (FIG. 9A) and PDGF (FIG. 9B).
Figure 9B:
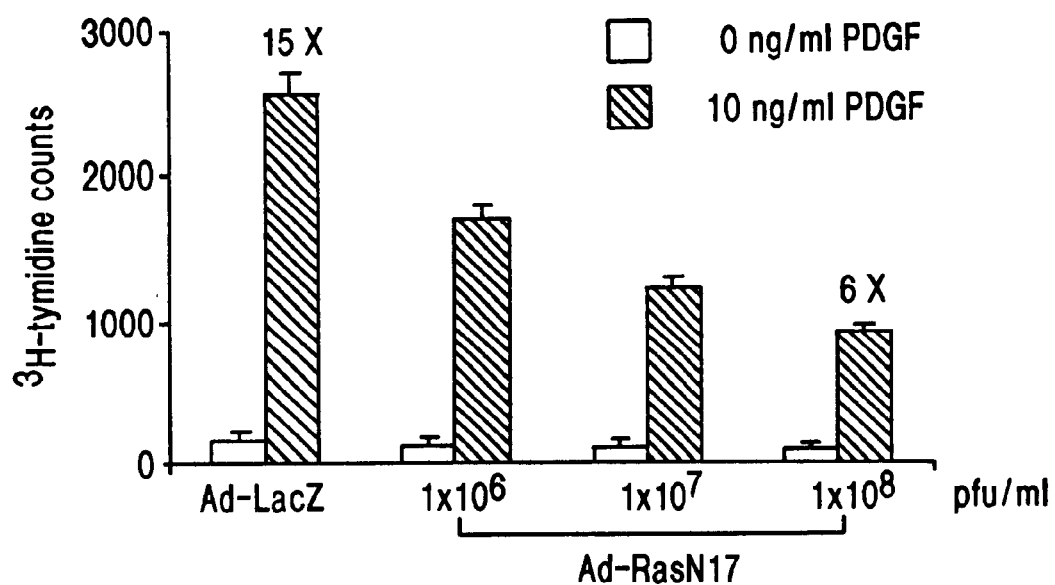

Serum-starved PSMCs infected with a replication-deficient virus carrying the RasN17 gene (Ad-RasN17) or the control replication-deficient virus carrying the lacZ gene (Ad-lacZ) were subjected to stimulation with 15% serum or 10 ng/nl PDGF. As shown in FIGS. 9A and 9B, $^3$H-thymidine incorporation assay showed that cell proliferation increased by 48 times in the serum-stimulated PSMCs and 15 times in the PDGF-stimulated PSMCs infected with Ad-lacZ ($10^8$ pfu/ml) as controls. In contrast, the serum- and PDGF-stimulated proliferation was reduced drastically for PSMCs infected with Ad-RasN17 at $10^8$ pfu/ml. These results indicate that expression of RasN17 in SMC can significantly attenuate the growth of the cells.

EXAMPLE 16

Use of Ras N17 in Gene Therapy to Prevent Artery Restenosis in vivo

Percutaneous transluminal coronary angioplasty (PTCA) has been extensively used as a clinical approach to treat coronary heart disease. However, restenosis occurs at the site of angioplasty in approximately one third of the patents within 6 months after PTCA. An important factor in restenosis is that the abrasive actions on the vessel wall during the PTCA procedure denude the endothelial cells and traumatize the vessel media, leading to the inflammatory and proliferative responses of smooth muscle cells to cause restenosis. Our in vitro studies on culture pig smooth muscle cells showed that the introduction of RasN17, a dominant negative mutant of p21Ras, into those cells inhibited the expression of genes that lead to cell proliferation in response to several mitogens (e.g., PDGF) and hemodynamic force (e.g. shear stress). These data led us to perform animal experiments to test the in vivo efficacy of negative mutants in the Ras pathway in preventing restenosis after PTCA. The aim is to provide an effective method for the reduction of the high incidence of restenosis after angioplasty and other surgical interventions in patients with coronary heart disease. Our results show that the restenosis of rat common carotid arteries after balloon injury is inhibited by local treatment with recombinant adenovirous carrying RasN17.

Animal Experiments

The rats were anesthetized with Ketamine (100 mg/kg body weight, i.p.) and Xylazine (10 mg/kg body weight, i.p.). Under sterile conditions, a neck incision was made and the left carotid artery was exposed. The common carotid artery (CCA) was clamped at 2 cm proximal to the bifurcation, and the internal carotid artery (ICA) was also clamped at its proximal position. The external carotid artery (ECA) was ligated at 1 cm distal to the bifurcation and a small arteriotomy was made just proximal to the ligation site for the insertion of a balloon catheter into the CCA. Vascular injury was achieved by inflating the balloon at 1.8 ATM, and then sliding the balloon catheter back and forth three times. After the deflation of the balloon and the withdrawal of the catheter, a vascular clamp was placed at 1 cm proximal to the bifurcation, and adenovirus (50 µl, $10^9$ pfu/ml) was injected through the arteriotomy into the segment distal to the clamp. After 15-min incubation, the virus was removed, and the clamp was removed to restore blood flow. The neck incision was closed, and the rat was allowed to recover with normal husbandry procedures for two weeks. Then, the animal was sacrificed with an overdose of anesthesia and perfused with PBS and 4% para-formaldehyde phosphate buffer at 100 mmHg for 10–15 min. The CCA was removed and fixed overnight for histological staining with hemtaoxylin-eosin.

Ad-RasN17 Inhibits Restenosis in the Rat Model After Balloon Injury

Figure 10A:
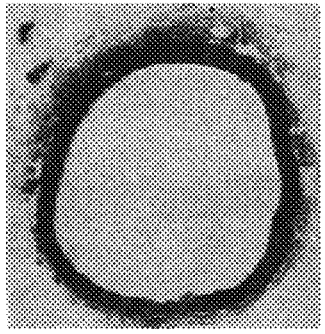
FIGS. 10A, 10B and 10C. Ad-RasN17 prevents restenosis in balloon injured rats Representative cross-sections from common carotid artery of rats.
Figure 10B:
Figure 10C:
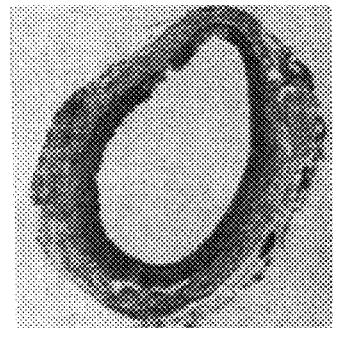
Figure 14:
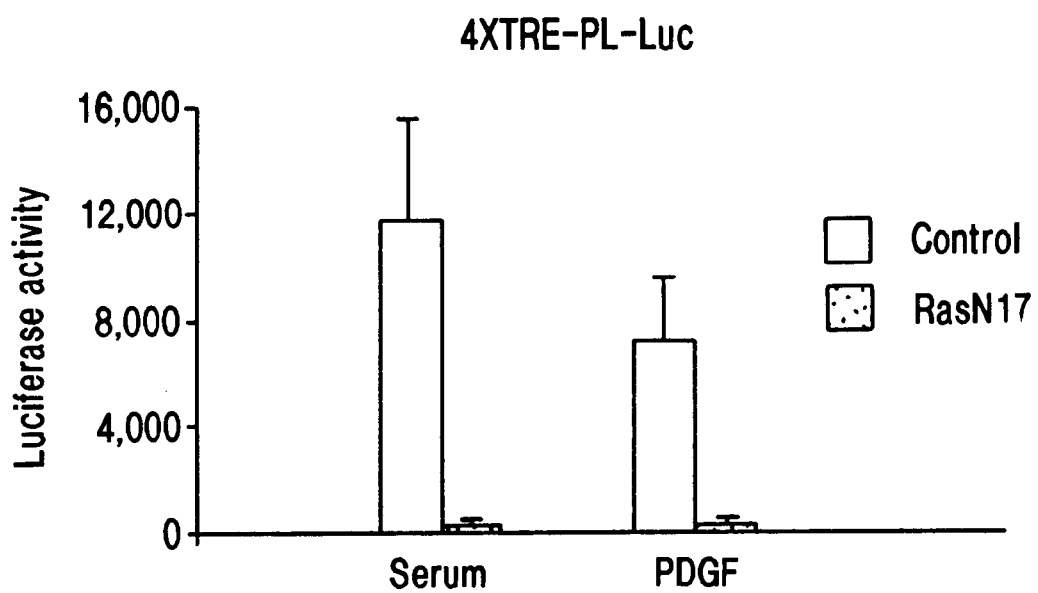
FIG. 14. RasN17 inhibits the serum- and PDGF- induced AP/1/TRE in bovine aortic endothelial cells.

The balloon procedures in the common carotid arteries of ten rats was performed with Ad-RasN17 or Ad-LacZ injected into the distal segment of the vessel. Ad-RasN17 was injected in five of the animals as the experimental group, and Ad-LacZ in the other five as controls. Histological examination was made to determine the intimal/media cross-sectional area ratio (I/M ratio) for the assessment of restenosis. In the control group, two of the five animals developed restenosis in both the proximal and distal segments (FIG 10B), and the I/M ratio was 1.99±0.23. In the experimental group, restenosis developed in two of the five animals, but only in the proximal, untreated segment of their vessels; the I/M ratio there was not significantly different from that in the control group. The distal segments of these experimental animals, where Ad-RasN17 injection was made, showed little evidence of restenosis (FIG. 10C), and the I/M ratio (0.95±1.15) was markedly lower than that in the proximal segment of the same animals or the segments in the control group. These results suggest that Ad-RasN17 is a potential therapeautical gene for the prevention of post angioplasty restenosis.

The expression of RasN17 in porcine muscle cells in vitro significantly attenuates cell proliferation in response to growth stimulations. The administration of RasN17 into rat common carotid arteries markedly reduced the restenosis of the vessel after balloon injury in vivo. Therefore, Ad-RasN17 is a potential therapeutical gene for the prevention of post angioplasty restenosis.

EXAMPLE 17

Use of RasN17 Derivatives as Therapeutic Gene in the Prevention of Restenosis

A partial sequence of RasN17 containing the mutated GTP binding site is postulated to be sufficient to be functional in inhibiting the proliferation of smooth muscle cells after PTCA. This truncated gene contains the 80 amino acids at the NH$_2$-terminal of RasN17 with the sequence shown below (SEQ ID NO:25):

MTEYKLVVVGAGGVGKNALTIQLIQN-HFVDEYDPTIEDSYRKQVVIDGETCLLDILDTAGL EEYSAMRDQSMRTGEGFLC

In addition, several mutants, e.g., RasA17, RasG17, and RasK17 in which Ser-17 in the wild-type is replaced by Ala, Gly, or Lys, respectfully, will be constructed (see table below for coding sequence). These mutants will be tested for their therapeutic effects in prevention of restenosis after PTCA.

| Amino Acid | Nucleotide Sequence |
|---|---|
| Ala(A) | GCT; GCC; CGA; GCG |
| Gly(G) | GGT; GGC; GGA; GGG |
| Lys(K) | AAG; AAA |

EXAMPLE 18

Restenosis After Balloon Procedures in Porcine Femoral Artery

Figure 15A:
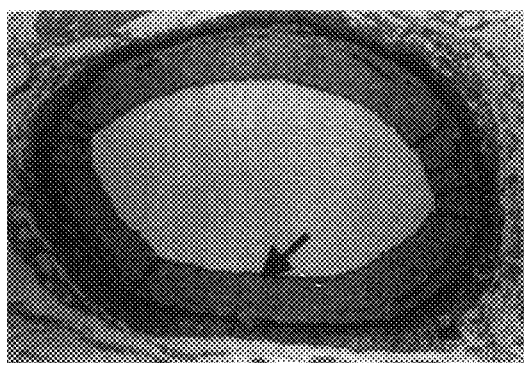
FIG. 15A and FIG. 15B. Representative cross-sections of the normal femoral artery (15A) and the balloon injured one (15B) 40 days after angioplasty.
Figure 15B:
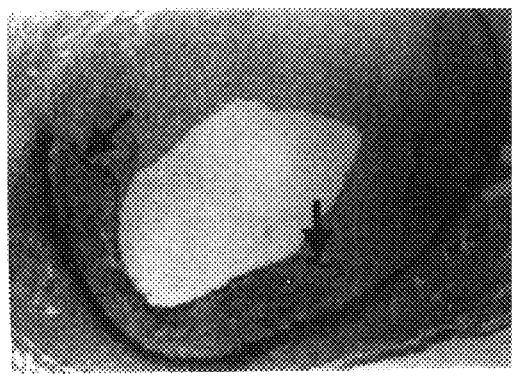

Balloon procedures in femoral arteries of two pigs have been performed. Restenosis was found in both of the animals 40 days after the procedures. Cross-sectional histology of the arterial specimen showed that the injured vessels were occluded (compare the normal artery in the left panel to the injured one in the right panel of FIG. 15). Experiments with Ad-RasN17 injection are currently conducted to investigate the inhibitory effects on restenosis.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Angel, P., and M. Karin. "The Role of Jun, Fos and the Ap-1 Complex in Cell-Proliferaton and Transformation." *Bioch. Biophys. Acta,* 1072:129–157, 1991.
2. Bogoyevitch, et al., "Ischemia and Reperfusion Activates Jun N-Termninal Protein Kinase (JNKs) in the Adult Rat Ventricular Myocardium," *Circulation,* 92:1–571, 1995.
3. Boguski, et al, "Proteins Regulating Ras and its Relatives," *Nature,* 366:643–654, 1993.
4. Chardin, et al., "Human Sos1: A Guanine Nucleotide Exchange Factor for Ras That Binds to GRB2," *Science,* 260:1338–1343, 1988.
5. Cobb, et al., "Extracellular Signal Regulated Kinases: ERKs in Progress," *Cell Regul.,* 2:965–978, 1991.
6. Coso, et al., "The Small GTP-Binding Proteins Rac1 and Cdc42 Regulate the Activity of the JNK/SAPK Signaling Pathway," *Cell,* 8:1137–1146, 1995.
7. Davies, P. F., "Flow-Mediated Endothelial Mechanotransduction," *Phsiol Rev.,* 75:519–560, 1995.
8. Davies, et al., "Quantitative Studies of Endothlial Cell Adhesion. Directional Remodeling of Focal Adhesion Sites in Response to Flow Forces," *J. Clin. Invest.,* 93:2031–2038, 1994.
9. Deng, et al., "c-Fos Transcriptional Activity Stimulated by H-Ras-Activated Protein Kinase Distinct from JNK and ERK," *Nature,* 371:171–175, 1994.
10. Derijard, et al., "JNK1: A Protein Kinase Stimulated by UV Light and Ha-Ras That Binds and Phosphorylates te c-Jun Activation Domain," *Cell,* 76:1025–1037, 1994.
11. DeVries-Smits, et al, "Involvement of $p21^{ras}$ in Activation of Extracellular Signal-Regulated Kinase 2," *Nature,* 357:602–604, 1992.
12. Downward, et al., "Stimulation of p21ras Upon T-cell Activation, *Nature,* 346:719–723, 1990.
13. Egan, et al., "Association of Sos Ras Exchange Protein with Grb2 is Implicated in Tyrosine Kinasse Signal Transduction and Transformation, *Nature,* 363:45–51, 1993.
14. Feig, et al., "Inhibition of NIH 3T3 Cell Proliferation by a Mutant ras Protein with Preferential Affinity for GDP," *Mol. Cell. Biol.,* 8:3235–3242, 198.
15. Frangos, et al., "Flow Effects on Prostacyclin Production by Cultured Human Endothelial Cells," *Science,* 227:1477–1479, 1985.
16. Frost, et al., "A Requirement for Extracellular Signal-Regulated Kinase (ERK) Function in the Activation of AP- by Ha-Ras, Phorbol 12-Myristate 13-Acetate, and Serum," *Proc. Natl. Acad. Sci., USA,* 91:3844–3848, 1994.
17. Galcheva-Gargova, et al, "an Osmosensing Signal Transduction Pathway in Mammalian Cells," *Science,* 265:806–808, 1994.
18. Gille, et al., "Phosphorylation of p62 TCF by MAP Kinase Stimulates Ternary Complex Formation at c-Fos Promotor," *Nature,* 358:414–417, 1992.
19. Hibi, et al., "Identification of an Oncoprotein and UV Responsive Protein Kinase That Binds and Potentiates the c-Jun Activation Domain," *Genes Dev.,* 7:2135–2148, 1993.
20. Hill, et al., "Transcriptional Regulation by Extracellular Signals: Mechanisms and Specificity," *Cell,* 80:199–211, 1995.
21. Hsieh, et al., "Shear-Induced Platelet-Derived Growth Factor Gene Expression in Human Endothelial Cells is Mediated by Protein Kinase C," *J. Cell Physiol.,* 150:552–558, 1992.
22. Hsieh, et al., "Pulsatile and Steady Flow Induces c-Fos Expression in Human Endothelial Cells," *J. Cell Physiol.,* 154:143–151, 1993.
23. Indolfi, et al. *Nature Medicine,* 1(6):541–545, 1995.
24. Kim, et al., "The TRE-Mediated Gene Expression in Response to Shear Stress Involves SH2-Containing Molecules," *FASEB J.,* 10:A24.
25. Kolch, et al., "Raf-1 Protein Kinase is Required for Growth of Induced NIH/3T3 Cells,' *Nature,* 349:426–428, 1991.
26. Kuchan, et al., "Role of G Proteins in Shear Stress-Mediated Nitric Oxide Production by Endothelial Cells," *Am. J. Physiol.,* 267(3 Pt 1):C753–758, 1994.
27. Kyriakis, et al., "The Stress-Activated Protein Kinase Subfamily of c-Jun Kinases," *Nature,* 369:156–160, 1994.
28. Lange-Carter, et al., "Ras-Dependent Growth Factor Regulation of MEK Kinase in PC12 Cells," *Science,* 265:1458–1461, 1994.
29. Leevers, et al., "Requirement for Ras in Raf Activation is Overcome by Targeting Raf to the Plasma Membrane," *Nature,* 372:739–745, 1994.
30. Lin, et al., "Identification of a Dual Specificity Kinase That Activates the Jun Kinases and p38-Mpk2," *Science,* 268:286–290, 1995.
31. Marais, et al., "The SRF Accessory Protein ELS-1 Contains a Growth Factor Regulated Transcription Domain," *Cell,* 73:381–393, 1993.
32. Marshall, C. J., "Specificity of Receptor Tyrosine Kinase Signaling: Transient Versus Sustained Extracellular Signal-Regulated Kinase Activation," *Cell,* 80:179–185, 1995.

33. Minden, et al., "Differential Activation of ERK and JNK Mitogen-Activated Protein Kinases by Raf-1 and MEKK," *Science,* 266:1719–1723, 1994.
34. Minden, et al., "c-Jun N-Terminal Phosphorylation Correlates with Activation of the JNK Subgroup But Not the ERK Subgroup of Mitogen-Activated Protein Kinases," *Mol. Cell. Biol.,* 14:6683–6688, 1994.
35. Minden, et al., "Selective Activation of the JNK Signaling Cascade and c-Jun Transcriptional Activity by the Small GTPases Rac and Cdc-42Hs," *Cell,* 81:1147–1157, 1995.
36. Morooka, et al., "Ischmia and Reperfusion Target ATF-2 and c-Jun to cAMP Response Elements and o an AP-1 Site From the c-Jun Promoter by Activating an ATF-2 Kinase," *Circulation,* 92:1–371, 1995.
37. Robbins, et al., "Regulation and Properties of Extracellular Signal-Regulated Protein Kinases 1 and 2 in vitro," *J. Biol. Chem.,* 268:5097–5106, 1993.
38. Rozengurt, E., "Growth Factors and Cell Proliferation," *Curr. Opin. Cell Biol.,* 4:161–165, 1992.
39. Russell, et al., "Direct Interaction between Ras and the Kinase Domain of Mitogen-Activate Protein Kinase Kinase Kinase (MEKK1)," *J. Biol. Chem.,* 270:11757–11760, 1995.
40. Sakaue, et al., "A Dominant-Negative Mutant of mSOS1 Inhibits Insulin-Induced Ras Activation and Reveals Ras-Dependen and -independent Insulin Signaling Pathways," *Mol. Cell. Biol.,* 15:379–388, 1995.
41. Shyy, et al., "Fluid Shear Stress Induces a Biphasic Response of Human Monocyte Chemotacic Protein-1 Gene Expression in Vascular Endothelium," *Proc. Natl. Acad. Sci. USA,* 91:4678–4682, 1994.
42. Shyy, et al., "The cis-Acting Phorbol Ester "12-O-Tetradecanoylphorbol 13-Acetate"-Responsive Element is Involved in Shear Stress-Induced Monocyte Chemotactic Protein 1 Gene Expression."
43. Sluss, et al., "Signal Transduction by Tumor Necrosis Factor Mediated by JNK Proten Kinases," *Mol. Cell. Biol.,* 14:8376–8384, 1994.
44. Stokoe, et al., "Activation of Raf as a Result of Recruitment of the Plasma Membrance," *Science,* 264:1463–1467, 1994.
45. Su, et al., "JNK is Involved in Signal Integration During Costimulation of T Lymphocytes," *Cell,* 77:727–736, 1994.
46. Taverse, et al., "Sustained Activation of te Mitogen-Activated Protein (MAP) Kinase Cascade may be Required for Differentiation of PC12 Cells. Comparison of the Effects of Nerve Growth Factor and Epidermal Growth Factor," *Biochem. J.,* 288:351–355, 1992.
47. Thomas, et al., "Ras is Essential for Nerve Growth Factor-and Phorbol Este-Induced Tyrosine Phosphorylation of MAP Kinases," *Cell,* 68:1031–1040, 1992.
48. Wang, et al., "Mechanotransduction Across the Cell Surface and Through the Cytoskeleton," *Science,* 260:1124–1127, 1993.
49. Yan, et al., "Activation of Stress-Activated Protein Kinase by MEKK1 Phosphorylation of its Activator SEK1, " *Nature,* 372:798–800, 1994.

What is claimed is:

1. A method of inhibiting the proliferation of Ras signal transduction pathway-dependent vascular smooth muscle cells at an angioplasty site, said method comprising:

delivering to vascular smooth muscle cells at an angioplasty site by catheter or luminal injection a mutant Ras nucleic acid encoding a mutant Ras protein, thereby inhibiting the proliferation of Ras signal transduction pathway-dependent vascular smooth muscle cells, wherein the nucleic acid is delivered in a replication defective adenovirus carrier, wherein the mutant Ras protein contains an amino acid sequence from residue 1 to residue 25 of the amino acid sequence at FIG. 12 (SEQ ID NO:3), wherein residue 17 is glycine or lysine, and wherein said mutant Ras protein inhibits Ras-mediated phosphorylation, thereby blocking a Ras signal transduction pathway.

2. The method of claim 1 wherein the catheter is a balloon catheter.

3. A method of inhibiting the occurrence of Ras signal transduction pathway-dependent restenosis resulting from an angioplasty procedure, said method comprising:

delivering by catheter or luminal injection to the angioplasty site a mutant Ras nucleic acid encoding a mutant Ras protein, thereby inhibiting the occurrence of Ras signal transduction pathway-dependent restenosis resulting from an angioplasty procedure, wherein said mutant Ras protein contains an amino acid sequence from residue 1 to residue 25 of the amino acid sequence at FIG. 12 (SEQ ID NO:3), wherein residue 17 is glycine or lysine, wherein the nucleic acid is delivered in a replication defective adenovirus carrier, and wherein said mutant Ras protein inhibits Ras-mediated phosphorylation, thereby blocking a Ras signal transduction pathway.

4. The method of claim 3 wherein the catheter is a balloon catheter.

5. The method of claim 3 wherein the delivering by catheter or luminal injection to the angioplasty site occurs during an angioplasty procedure.

* * * * *

SEQUENCE LISTING

<160> NUMBER OF SEQ ID NOS: 25

<210> SEQ ID NO 1
<211> LENGTH: 8
<212> TYPE: DNA
<213> ORGANISM: Rattus norvegicus
<220> FEATURE:
<221> NAME/KEY: misc_feature
<222> LOCATION: (0)...(0)
<223> OTHER INFORMATION: Responsive element in the 5' promoter region of the MCP-1 gene.

<400> SEQUENCE: 1 tgactaca                                                                8

<210> SEQ ID NO 2
<211> LENGTH: 570
<212> TYPE: DNA
<213> ORGANISM: Rattus norvegicus
<220> FEATURE:
<221> NAME/KEY: CDS
<222> LOCATION: (1)...(570)

<400> SEQUENCE: 2

```
atg acg gaa tat aag ctg gtg gtg gtg ggc gcc ggc ggt gtg ggc aaa        48
Met Thr Glu Tyr Lys Leu Val Val Val Gly Ala Gly Gly Val Gly Lys
  1               5                  10                  15 aat gcg ctg acc atc cag ctg atc cag aac cat ttt gtg gac gaa tac        96
Asn Ala Leu Thr Ile Gln Leu Ile Gln Asn His Phe Val Asp Glu Tyr
             20                  25                  30 gac ccc act ata gag gat tcc tac cgg aag cag gtg gtc att gat ggg       144
Asp Pro Thr Ile Glu Asp Ser Tyr Arg Lys Gln Val Val Ile Asp Gly
```

```
                    35                  40                  45
gag acg tgc ctg ttg gac atc ctg gat acc gcc ggc ctg gag gag tac        192
Glu Thr Cys Leu Leu Asp Ile Leu Asp Thr Ala Gly Leu Glu Glu Tyr
         50                  55                  60 agc gcc atg cgg gac cag tca atg cgc acc ggg gag ggc ttc ctg tgt        240
Ser Ala Met Arg Asp Gln Ser Met Arg Thr Gly Glu Gly Phe Leu Cys
 65                  70                  75                  80 gtg ttt gcc atc aac aac acc aag tct ttt gag gac atc cac cag tac        288
Val Phe Ala Ile Asn Asn Thr Lys Ser Phe Glu Asp Ile His Gln Tyr
                 85                  90                  95 agg gag cag atc aaa cgg gtg aag gac tcg gat gac gtg ccc atg gtg        336
Arg Glu Gln Ile Lys Arg Val Lys Asp Ser Asp Asp Val Pro Met Val
             100                 105                 110 ctg gtg ggg aac aag tgt gac ctg gct gca cgc act gtg gaa tct cgg        384
Leu Val Gly Asn Lys Cys Asp Leu Ala Ala Arg Thr Val Glu Ser Arg
             115                 120                 125 cag gct cag gac ctc gcc cga agc tac ggc atc ccc tac atc gag acc        432
Gln Ala Gln Asp Leu Ala Arg Ser Tyr Gly Ile Pro Tyr Ile Glu Thr
         130                 135                 140 tcg gcc aag acc cgg cag gga gtg gag gat gcc ttc tac acg ttg gtg        480
Ser Ala Lys Thr Arg Gln Gly Val Glu Asp Ala Phe Tyr Thr Leu Val
145                 150                 155                 160 cgt gag atc cgg cag cac aag ctg cgg aag ctg aac cct cct gat gag        528
Arg Glu Ile Arg Gln His Lys Leu Arg Lys Leu Asn Pro Pro Asp Glu
                 165                 170                 175 agt ggc ccc ggc tgc atg agc tgc aag tgt gtg ctc tcc tga                570
Ser Gly Pro Gly Cys Met Ser Cys Lys Cys Val Leu Ser
             180                 185

<210> SEQ ID NO 3
<211> LENGTH: 189
<212> TYPE: PRT
<213> ORGANISM: Rattus norvegicus

<400> SEQUENCE: 3

Met Thr Glu Tyr Lys Leu Val Val Gly Ala Gly Gly Val Gly Lys
  1               5                  10                  15

Asn Ala Leu Thr Ile Gln Leu Ile Gln Asn His Phe Val Asp Glu Tyr
                 20                  25                  30

Asp Pro Thr Ile Glu Asp Ser Tyr Arg Lys Gln Val Val Ile Asp Gly
             35                  40                  45

Glu Thr Cys Leu Leu Asp Ile Leu Asp Thr Ala Gly Leu Glu Glu Tyr
         50                  55                  60

Ser Ala Met Arg Asp Gln Ser Met Arg Thr Gly Glu Gly Phe Leu Cys
 65                  70                  75                  80

Val Phe Ala Ile Asn Asn Thr Lys Ser Phe Glu Asp Ile His Gln Tyr
                 85                  90                  95

Arg Glu Gln Ile Lys Arg Val Lys Asp Ser Asp Asp Val Pro Met Val
             100                 105                 110

Leu Val Gly Asn Lys Cys Asp Leu Ala Ala Arg Thr Val Glu Ser Arg
             115                 120                 125

Gln Ala Gln Asp Leu Ala Arg Ser Tyr Gly Ile Pro Tyr Ile Glu Thr
         130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                 165                 170                 175
```

```
Ser Gly Pro Gly Cys Met Ser Cys Lys Cys Val Leu Ser
            180                 185

<210> SEQ ID NO 4
<211> LENGTH: 80
<212> TYPE: PRT
<213> ORGANISM: Rattus norvegicus
<220> FEATURE:
<221> NAME/KEY: VARIANT
<222> LOCATION: (0)...(0)
<223> OTHER INFORMATION: Xaa = Any Amino Acid, except for Serine.

<400> SEQUENCE: 4

Met Thr Glu Tyr Lys Leu Val Val Gly Ala Gly Gly Val Gly Lys
 1               5                  10                  15

Xaa Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Leu Glu Glu Tyr
        50                  55                  60

Ser Ala Met Arg Asp Gln Ser Met Arg Thr Gly Glu Gly Phe Leu Cys
65                  70                  75                  80

<210> SEQ ID NO 5
<211> LENGTH: 150
<212> TYPE: PRT
<213> ORGANISM: Rattus norvegicus
<220> FEATURE:
<221> NAME/KEY: VARIANT
<222> LOCATION: (0)...(0)
<223> OTHER INFORMATION: Xaa = Any Amino Acid, except for Serine

<400> SEQUENCE: 5

Met Thr Glu Tyr Lys Leu Val Val Gly Ala Gly Gly Val Gly Lys
 1               5                  10                  15

Xaa Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Leu Glu Glu Tyr
        50                  55                  60

Ser Ala Met Arg Asp Gln Ser Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
            100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
        130                 135                 140

Ser Ala Lys Thr Arg Gln
145                 150

<210> SEQ ID NO 6
<211> LENGTH: 189
<212> TYPE: PRT
<213> ORGANISM: Rattus norvegicus

<400> SEQUENCE: 6
```

```
Met Thr Glu Tyr Lys Leu Val Val Gly Ala Gly Val Gly Lys
1               5                   10                  15

Asn Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
                35                  40                  45

Glu Thr Cys Leu Leu Asp Ile Leu Asp Thr Ala Gly Leu Glu Glu Tyr
        50                  55                  60

Ser Ala Met Arg Asp Gln Ser Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
                100                 105                 110

Leu Val Gly Asn Lys Cys Asp Leu Ala Ala Arg Thr Val Glu Ser Arg
                115                 120                 125

Gln Ala Gln Asp Leu Ala Arg Ser Tyr Gly Ile Pro Tyr Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
                180                 185
```

<210> SEQ ID NO 7
<211> LENGTH: 160
<212> TYPE: PRT
<213> ORGANISM: Rattus norvegicus
<220> FEATURE:
<221> NAME/KEY: VARIANT
<222> LOCATION: (0)...(0)
<223> OTHER INFORMATION: Xaa = Any Amino Acid, except for Serine

<400> SEQUENCE: 7

```
Met Thr Glu Tyr Lys Leu Val Val Gly Ala Gly Gly Val Gly Lys
1               5                   10                  15

Xaa Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
                35                  40                  45

Glu Thr Cys Leu Leu Asp Ile Leu Asp Thr Ala Gly Leu Glu Glu Tyr
        50                  55                  60

Ser Ala Met Arg Asp Gln Ser Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
                100                 105                 110

Leu Val Gly Asn Lys Cys Asp Leu Ala Ala Arg Thr Val Glu Ser Arg
                115                 120                 125

Gln Ala Gln Asp Leu Ala Arg Ser Tyr Gly Ile Pro Tyr Ile Glu Thr
        130                 135                 140

Ser Ala Lys Thr Arg Gln Gly Val Glu Asp Ala Phe Tyr Thr Leu Val
145                 150                 155                 160
```

<210> SEQ ID NO 8
<211> LENGTH: 240
<212> TYPE: DNA
<213> ORGANISM: Rattus norvegicus
<220> FEATURE:
<221> NAME/KEY: misc_feature
<222> LOCATION: (49)...(51)
<223> OTHER INFORMATION: nnn = Any nucleic acid triplet, except for UCA, UCC, UCG, UCU, AGC, or AGU

<400> SEQUENCE: 8

```
atgacggaat ataagctggt ggtggtgggc gccggcggtg tgggcaaann ngcgctgacc     60
atccagctga tccagaacca ttttgtggac gaatacgacc ccactataga ggattcctac    120
cggaagcagg tggtcattga tggggagacg tgcctgttgg acatcctgga taccgccggc    180
ctggaggagt acagcgccat gcgggaccag tcaatgcgca ccggggaggg cttcctgtgt    240
```

<210> SEQ ID NO 9
<211> LENGTH: 480
<212> TYPE: DNA
<213> ORGANISM: Rattus norvegicus
<220> FEATURE:
<221> NAME/KEY: misc_feature
<222> LOCATION: (49)...(51)
<223> OTHER INFORMATION: nnn = Any nucleic acid triplet, except for UCA, UCC, UCG, UCU, AGC, or AGU

<400> SEQUENCE: 9

```
atgacggaat ataagctggt ggtggtgggc gccggcggtg tgggcaaann ngcgctgacc     60
atccagctga tccagaacca ttttgtggac gaatacgacc ccactataga ggattcctac    120
cggaagcagg tggtcattga tggggagacg tgcctgttgg acatcctgga taccgccggc    180
ctggaggagt acagcgccat gcgggaccag tcaatgcgca ccggggaggg cttcctgtgt    240
gtgtttgcca tcaacaacac caagtctttt gaggacatcc accagtacag ggagcagatc    300
aaacgggtga aggactcgga tgacgtgccc atggtgctgg tggggaacaa gtgtgacctg    360
gctgcacgca ctgtggaatc tcggcaggct caggacctcg cccgaagcta cggcatcccc    420
tacatcgaga cctcggccaa gacccggcag ggagtggagg atgccttcta cacgttggtg    480
```

<210> SEQ ID NO 10
<211> LENGTH: 450
<212> TYPE: DNA
<213> ORGANISM: Rattus norvegicus
<220> FEATURE:
<221> NAME/KEY: misc_feature
<222> LOCATION: (49)...(51)
<223> OTHER INFORMATION: nnn = Any nucleic acid triplet, except for UCA, UCC, UCG, UCU, AGC, or AGU

<400> SEQUENCE: 10

```
atgacggaat ataagctggt ggtggtgggc gccggcggtg tgggcaaann ngcgctgacc     60
atccagctga tccagaacca ttttgtggac gaatacgacc ccactataga ggattcctac    120
cggaagcagg tggtcattga tggggagacg tgcctgttgg acatcctgga taccgccggc    180
ctggaggagt acagcgccat gcgggaccag tcaatgcgca ccggggaggg cttcctgtgt    240
gtgtttgcca tcaacaacac caagtctttt gaggacatcc accagtacag ggagcagatc    300
aaacgggtga aggactcgga tgacgtgccc atggtgctgg tggggaacaa gtgtgacctg    360
gctgcacgca ctgtggaatc tcggcaggct caggacctcg cccgaagcta cggcatcccc    420
tacatcgaga cctcggccaa gacccggcag                                     450
```

<210> SEQ ID NO 11
<211> LENGTH: 570
<212> TYPE: DNA
<213> ORGANISM: Artificial Sequence
<220> FEATURE:
<221> NAME/KEY: misc_feature
<222> LOCATION: (49)...(51)
<223> OTHER INFORMATION: nnn = Any nucleic acid triplet, except for UCA, UCC, UCG, UCU, AGC, or AGU
<223> OTHER INFORMATION: Variation of SEQ ID NO.:2

<400> SEQUENCE: 11

```
atgacggaat ataagctggt ggtggtgggc gccggcggtg tgggcaaann ngcgctgacc      60
atccagctga tccagaacca ttttgtggac gaatacgacc ccactataga ggattcctac     120
cggaagcagg tggtcattga tggggagacg tgcctgttgg acatcctgga taccgccggc     180
ctggaggagt acagcgccat gcgggaccag tcaatgcgca ccggggaggg cttcctgtgt     240
gtgtttgcca tcaacaacac caagtctttt gaggacatcc accagtacag ggagcagatc     300
aaacgggtga aggactcgga tgacgtgccc atggtgctgg tggggaacaa gtgtgacctg     360
gctgcacgca ctgtggaatc tcggcaggct caggacctcc cccgaagcta cggcatcccc     420
tacatcgaga cctcggccaa gacccggcag ggagtggagg atgccttcta cacgttggtg     480
cgtgagatcc ggcagcacaa gctgcggaag ctgaaccctc ctgatgagag tggccccggc     540
tgcatgagct gcaagtgtgt gctctcctga                                      570
```

<210> SEQ ID NO 12
<211> LENGTH: 240
<212> TYPE: DNA
<213> ORGANISM: Artificial Sequence
<220> FEATURE:
<223> OTHER INFORMATION: Variation of SEQ ID NO.:2

<400> SEQUENCE: 12

```
atgacggaat ataagctggt ggtggtgggc gccggcggtg tgggcaaagc tgcgctgacc      60
atccagctga tccagaacca ttttgtggac gaatacgacc ccactataga ggattcctac     120
cggaagcagg tggtcattga tggggagacg tgcctgttgg acatcctgga taccgccggc     180
ctggaggagt acagcgccat gcgggaccag tcaatgcgca ccggggaggg cttcctgtgt     240
```

<210> SEQ ID NO 13
<211> LENGTH: 240
<212> TYPE: DNA
<213> ORGANISM: Artificial Sequence
<220> FEATURE:
<223> OTHER INFORMATION: Variation of SEQ ID NO.:2

<400> SEQUENCE: 13

```
atgacggaat ataagctggt ggtggtgggc gccggcggtg tgggcaaagg tgcgctgacc      60
atccagctga tccagaacca ttttgtggac gaatacgacc ccactataga ggattcctac     120
cggaagcagg tggtcattga tggggagacg tgcctgttgg acatcctgga taccgccggc     180
ctggaggagt acagcgccat gcgggaccag tcaatgcgca ccggggaggg cttcctgtgt     240
```

<210> SEQ ID NO 14
<211> LENGTH: 240
<212> TYPE: DNA
<213> ORGANISM: Artificial Sequence
<220> FEATURE:
<223> OTHER INFORMATION: Variation of SEQ ID NO.:2

<400> SEQUENCE: 14

-continued

```
atgacggaat ataagctggt ggtggtgggc gccggcggtg tgggcaaaaa ggcgctgacc      60
atccagctga tccagaacca ttttgtggac gaatacgacc ccactataga ggattcctac     120
cggaagcagg tggtcattga tggggagacg tgcctgttgg acatcctgga taccgccggc     180
ctggaggagt acagcgccat gcgggaccag tcaatgcgca ccggggaggg cttcctgtgt     240
```

<210> SEQ ID NO 15
<211> LENGTH: 18
<212> TYPE: DNA
<213> ORGANISM: Artificial Sequence
<220> FEATURE:
<223> OTHER INFORMATION: Primer sequence at the 5' end of the p21 Ras.

<400> SEQUENCE: 15

```
ttgtggacga atacgacc                                                    18
```

<210> SEQ ID NO 16
<211> LENGTH: 132
<212> TYPE: DNA
<213> ORGANISM: Artificial Sequence
<220> FEATURE:
<223> OTHER INFORMATION: Partial sequence of the cloned RasN17.

<400> SEQUENCE: 16

```
ctactcgagc gttacgaagg ttacttctgc tctaaagctc ggatcgataa gcttgcgcca      60
ggccggggcc gagcgatgac ggaatataag ctggtggtgg tgggcgccgg cggtgttggg     120
caagaatgcg ct                                                         132
```

<210> SEQ ID NO 17
<211> LENGTH: 25
<212> TYPE: PRT
<213> ORGANISM: Rattus norvegicus
<220> FEATURE:
<221> NAME/KEY: VARIANT
<222> LOCATION: (0)...(0)
<223> OTHER INFORMATION: Xaa = Any Amino Acid, except for Serine

<400> SEQUENCE: 17

```
Met Thr Glu Tyr Lys Leu Val Val Val Gly Ala Gly Gly Val Gly Lys
  1               5                  10                  15

Xaa Ala Leu Thr Ile Gln Leu Ile Gln
            20                  25
```

<210> SEQ ID NO 18
<211> LENGTH: 240
<212> TYPE: DNA
<213> ORGANISM: Artificial Sequence
<220> FEATURE:
<223> OTHER INFORMATION: Variation of SEQ ID NO.:2

<400> SEQUENCE: 18

```
atgacggaat ataagctggt ggtggtgggc gccggcggtg tgggcaaagc cgcgctgacc      60
atccagctga tccagaacca ttttgtggac gaatacgacc ccactataga ggattcctac     120
cggaagcagg tggtcattga tggggagacg tgcctgttgg acatcctgga taccgccggc     180
ctggaggagt acagcgccat gcgggaccag tcaatgcgca ccggggaggg cttcctgtgt     240
```

<210> SEQ ID NO 19
<211> LENGTH: 240
<212> TYPE: DNA
<213> ORGANISM: Artificial Sequence
<220> FEATURE:

<223> OTHER INFORMATION: Variation of SEQ ID NO.:2

<400> SEQUENCE: 19

```
atgacggaat ataagctggt ggtggtgggc gccggcggtg tgggcaaagc agcgctgacc    60
atccagctga tccagaacca ttttgtggac gaatacgacc ccactataga ggattcctac   120
cggaagcagg tggtcattga tggggagacg tgcctgttgg acatcctgga taccgccggc   180
ctggaggagt acagcgccat gcgggaccag tcaatgcgca ccggggaggg cttcctgtgt   240
```

<210> SEQ ID NO 20
<211> LENGTH: 240
<212> TYPE: DNA
<213> ORGANISM: Artificial Sequence
<220> FEATURE:
<223> OTHER INFORMATION: Variation of SEQ ID NO.:2

<400> SEQUENCE: 20

```
atgacggaat ataagctggt ggtggtgggc gccggcggtg tgggcaaagc ggcgctgacc    60
atccagctga tccagaacca ttttgtggac gaatacgacc ccactataga ggattcctac   120
cggaagcagg tggtcattga tggggagacg tgcctgttgg acatcctgga taccgccggc   180
ctggaggagt acagcgccat gcgggaccag tcaatgcgca ccggggaggg cttcctgtgt   240
```

<210> SEQ ID NO 21
<211> LENGTH: 240
<212> TYPE: DNA
<213> ORGANISM: Artificial Sequence
<220> FEATURE:
<223> OTHER INFORMATION: Variation of SEQ ID NO.:2

<400> SEQUENCE: 21

```
atgacggaat ataagctggt ggtggtgggc gccggcggtg tgggcaaagg cgcgctgacc    60
atccagctga tccagaacca ttttgtggac gaatacgacc ccactataga ggattcctac   120
cggaagcagg tggtcattga tggggagacg tgcctgttgg acatcctgga taccgccggc   180
ctggaggagt acagcgccat gcgggaccag tcaatgcgca ccggggaggg cttcctgtgt   240
```

<210> SEQ ID NO 22
<211> LENGTH: 240
<212> TYPE: DNA
<213> ORGANISM: Artificial Sequence
<220> FEATURE:
<223> OTHER INFORMATION: Variation of SEQ ID NO.:2

<400> SEQUENCE: 22

```
atgacggaat ataagctggt ggtggtgggc gccggcggtg tgggcaaagg agcgctgacc    60
atccagctga tccagaacca ttttgtggac gaatacgacc ccactataga ggattcctac   120
cggaagcagg tggtcattga tggggagacg tgcctgttgg acatcctgga taccgccggc   180
ctggaggagt acagcgccat gcgggaccag tcaatgcgca ccggggaggg cttcctgtgt   240
```

<210> SEQ ID NO 23
<211> LENGTH: 240
<212> TYPE: DNA
<213> ORGANISM: Artificial Sequence
<220> FEATURE:
<223> OTHER INFORMATION: Variation of SEQ ID NO.:2

<400> SEQUENCE: 23

```
atgacggaat ataagctggt ggtggtgggc gccggcggtg tgggcaaagg ggcgctgacc    60
atccagctga tccagaacca ttttgtggac gaatacgacc ccactataga ggattcctac   120
```

```
cggaagcagg tggtcattga tggggagacg tgcctgttgg acatcctgga taccgccggc    180
ctggaggagt acagcgccat gcgggaccag tcaatgcgca ccggggaggg cttcctgtgt    240

<210> SEQ ID NO 24
<211> LENGTH: 240
<212> TYPE: DNA
<213> ORGANISM: Artificial Sequence
<220> FEATURE:
<223> OTHER INFORMATION: Variation of SEQ ID NO.:2

<400> SEQUENCE: 24
atgacggaat ataagctggt ggtggtgggc gccggcggtg tgggcaaaaa agcgctgacc     60
atccagctga tccagaacca ttttgtggac gaatacgacc ccactataga ggattcctac    120
cggaagcagg tggtcattga tggggagacg tgcctgttgg acatcctgga taccgccggc    180
ctggaggagt acagcgccat gcgggaccag tcaatgcgca ccggggaggg cttcctgtgt    240

<210> SEQ ID NO 25
<211> LENGTH: 80
<212> TYPE: PRT
<213> ORGANISM: Artificial Sequence
<220> FEATURE:
<223> OTHER INFORMATION: Derivative of PCR product

<400> SEQUENCE: 25

Met Thr Glu Tyr Lys Leu Val Val Val Gly Ala Gly Gly Val Gly Lys
 1               5                  10                  15

Asn Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Leu Glu Glu Tyr
        50                  55                  60

Ser Ala Met Arg Asp Gln Ser Met Arg Thr Gly Glu Gly Phe Leu Cys
65                  70                  75                  80
```